US012303105B2

(12) United States Patent
Binmoeller et al.

(10) Patent No.: US 12,303,105 B2
(45) Date of Patent: May 20, 2025

(54) LUMINAL STRUCTURE ANCHORING DEVICES AND METHODS

(71) Applicant: Boston Scientific Scimed, Inc., Maple Grove, MN (US)

(72) Inventors: Kenneth F. Binmoeller, San Francisco, CA (US); Corbett W. Stone, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/517,164

(22) Filed: Nov. 22, 2023

(65) Prior Publication Data
US 2024/0090749 A1    Mar. 21, 2024

Related U.S. Application Data

(63) Continuation of application No. 17/412,385, filed on Aug. 26, 2021, now Pat. No. 11,857,160, which is a
(Continued)

(51) Int. Cl.
*A61B 17/11* (2006.01)
*A61B 1/00* (2006.01)
(Continued)

(52) U.S. Cl.
CPC ........ *A61B 1/00148* (2022.02); *A61B 1/0014* (2013.01); *A61B 1/041* (2013.01);
(Continued)

(58) Field of Classification Search
CPC . A61B 17/11; A61B 17/0401; A61B 17/0469; A61B 17/1114;
(Continued)

(56) References Cited

U.S. PATENT DOCUMENTS 2,127,903 A    8/1938    Bowen
3,039,468 A    6/1962    Price
(Continued)

FOREIGN PATENT DOCUMENTS

AU    665964 B2    1/1996
AU    2011202408 A1    6/2011
(Continued)

OTHER PUBLICATIONS

Swain et al., Knot trying at flexible endoscopy, Gastrointestinal Endoscopy, 40(6), pp. 722-729, Nov. 1994.
(Continued)

*Primary Examiner* — Tuan V Nguyen
(74) *Attorney, Agent, or Firm* — Seager, Tufte & Wickhem, LLP

(57) ABSTRACT

The present invention relates to a device for endoscopy or endosonography-guided transluminal interventions whereby two luminal structures in the body may be drawn toward each other and a fluid conduit formed in between. The device may have a hollow central member to which is coupled a distal retention member and in one embodiment a proximal retention member. The retention members may each be positioned inside one of the luminal structures and expanded from a first condition to an expanded second condition having an increased radius. The length of the central member may be shortened and its diameter expanded to approximate the two retention members and thereby the luminal structures.

20 Claims, 28 Drawing Sheets

Related U.S. Application Data continuation of application No. 15/331,151, filed on Oct. 21, 2016, now Pat. No. 11,134,949, which is a continuation of application No. 13/865,098, filed on Apr. 17, 2013, now Pat. No. 10,945,735, which is a continuation of application No. 11/867,636, filed on Oct. 4, 2007, now Pat. No. 8,425,539, which is a continuation-in-part of application No. 10/822,138, filed on Apr. 12, 2004, now abandoned.

(51) Int. Cl.
    *A61B 1/04*     (2006.01)
    *A61B 17/04*     (2006.01)
    *A61B 17/00*     (2006.01)
    *A61N 1/05*     (2006.01)
    *A61N 1/36*     (2006.01)

(52) U.S. Cl.
    CPC ...... *A61B 17/0401* (2013.01); *A61B 17/0469* (2013.01); *A61B 17/11* (2013.01); *A61B 2017/00867* (2013.01); *A61B 2017/0408* (2013.01); *A61B 2017/0409* (2013.01); *A61B 2017/0414* (2013.01); *A61B 2017/0454* (2013.01); *A61B 2017/0464* (2013.01); *A61B 17/1114* (2013.01); *A61B 2017/1139* (2013.01); *A61N 1/05* (2013.01); *A61N 1/36007* (2013.01); *A61N 1/3601* (2013.01)

(58) Field of Classification Search
    CPC .. A61B 2017/00867; A61B 2017/1103; A61B 2017/1107; A61B 2017/1139; A61F 2/06; A61F 2/064
See application file for complete search history.

(56) References Cited

U.S. PATENT DOCUMENTS

| | | |
|---|---|---|
| 3,717,151 A | 2/1973 | Collett |
| 3,874,388 A | 4/1975 | King et al. |
| 3,970,090 A | 7/1976 | Loiacono |
| 4,173,392 A | 11/1979 | Ekinaka et al. |
| 4,235,238 A | 11/1980 | Ogiu et al. |
| 4,580,568 A | 4/1986 | Gianturco |
| 4,587,972 A | 5/1986 | Morantte, Jr. |
| 4,608,965 A | 9/1986 | Anspach et al. |
| 4,705,040 A | 11/1987 | Mueller et al. |
| 4,790,813 A | 12/1988 | Kensey |
| 4,869,263 A | 9/1989 | Segal et al. |
| 4,896,678 A | 1/1990 | Ogawa |
| 4,917,097 A | 4/1990 | Proudian et al. |
| 4,920,967 A | 5/1990 | Cottonaro et al. |
| 4,950,285 A | 8/1990 | Wilk |
| 4,973,317 A | 11/1990 | Bobrove |
| 4,990,139 A | 2/1991 | Jang |
| 5,021,059 A | 6/1991 | Kensey et al. |
| 5,024,655 A | 6/1991 | Freeman et al. |
| 5,061,275 A | 10/1991 | Wallsten et al. |
| 5,064,435 A | 11/1991 | Porter |
| 5,180,392 A | 1/1993 | Skeie et al. |
| 5,183,464 A | 2/1993 | Dubrul et al. |
| 5,197,971 A | 3/1993 | Bonutti |
| 5,207,229 A | 5/1993 | Winters |
| 5,209,727 A | 5/1993 | Radisch et al. |
| 5,211,651 A | 5/1993 | Reger et al. |
| 5,221,258 A | 6/1993 | Shturman |
| 5,224,945 A | 7/1993 | Pannek, Jr. |
| 5,226,421 A | 7/1993 | Frisbie et al. |
| 5,234,447 A | 8/1993 | Kaster et al. |
| 5,246,007 A | 9/1993 | Frisbie et al. |
| 5,246,445 A | 9/1993 | Yachia et al. |
| 5,257,990 A | 11/1993 | Nash |
| 5,258,000 A | 11/1993 | Gianturco |
| 5,261,920 A | 11/1993 | Main et al. |
| 5,275,610 A | 1/1994 | Eberbach |
| 5,275,611 A | 1/1994 | Behl |
| 5,282,824 A | 2/1994 | Gianturco |
| 5,290,249 A | 3/1994 | Foster et al. |
| 5,304,198 A | 4/1994 | Samson |
| 5,330,497 A | 7/1994 | Freitas et al. |
| 5,353,785 A | 10/1994 | Wilk |
| 5,368,595 A | 11/1994 | Lewis |
| 5,372,588 A | 12/1994 | Farley et al. |
| 5,381,788 A | 1/1995 | Matula et al. |
| 5,387,235 A | 2/1995 | Chuter |
| 5,395,349 A | 3/1995 | Quiachon et al. |
| 5,415,664 A | 5/1995 | Pinchuk |
| 5,417,687 A | 5/1995 | Nardella et al. |
| 5,425,739 A | 6/1995 | Jessen |
| 5,443,484 A | 8/1995 | Kirsch et al. |
| 5,445,794 A | 8/1995 | Wihlborg |
| 5,449,355 A | 9/1995 | Rhum et al. |
| 5,458,131 A | 10/1995 | Wilk |
| 5,462,561 A | 10/1995 | Voda |
| 5,470,337 A | 11/1995 | Moss |
| 5,495,851 A | 3/1996 | Dill et al. |
| 5,496,311 A | 3/1996 | Abele et al. |
| 5,520,700 A | 5/1996 | Beyar et al. |
| 5,531,699 A | 7/1996 | Tomba et al. |
| 5,536,248 A | 7/1996 | Weaver et al. |
| 5,588,432 A | 12/1996 | Crowley |
| 5,601,588 A | 2/1997 | Tonomura et al. |
| 5,603,698 A | 2/1997 | Roberts et al. |
| 5,620,456 A | 4/1997 | Sauer et al. |
| 5,620,457 A | 4/1997 | Pinchasik et al. |
| 5,632,762 A | 5/1997 | Myler |
| 5,662,664 A | 9/1997 | Gordon et al. |
| 5,681,345 A | 10/1997 | Euteneuer |
| 5,688,247 A | 11/1997 | Haindl et al. |
| 5,697,944 A | 12/1997 | Lary |
| 5,702,418 A | 12/1997 | Ravenscroft |
| 5,709,671 A | 1/1998 | Stephens et al. |
| 5,709,703 A | 1/1998 | Lukic et al. |
| 5,709,707 A | 1/1998 | Lock et al. |
| 5,709,713 A | 1/1998 | Evans et al. |
| 5,713,870 A | 2/1998 | Yoon |
| 5,716,325 A | 2/1998 | Bonutti |
| 5,725,552 A | 3/1998 | Kotula et al. |
| 5,776,101 A | 7/1998 | Goy |
| 5,797,906 A | 8/1998 | Rhum et al. |
| 5,817,062 A | 10/1998 | Flom et al. |
| 5,827,276 A | 10/1998 | Leveen et al. |
| 5,830,222 A | 11/1998 | Makower |
| 5,843,116 A | 12/1998 | Crocker et al. |
| 5,843,127 A | 12/1998 | Li |
| 5,853,421 A | 12/1998 | Leschinsky et al. |
| 5,853,422 A | 12/1998 | Huebsch et al. |
| 5,855,576 A | 1/1999 | Leveen et al. |
| 5,857,999 A | 1/1999 | Quick et al. |
| 5,858,006 A | 1/1999 | Van et al. |
| 5,882,340 A | 3/1999 | Yoon |
| 5,893,856 A | 4/1999 | Jacob et al. |
| 5,897,567 A | 4/1999 | Ressemann et al. |
| 5,935,107 A | 8/1999 | Taylor et al. |
| 5,944,738 A | 8/1999 | Amplatz et al. |
| 5,951,576 A | 9/1999 | Wakabayashi |
| 5,951,588 A | 9/1999 | Moenning |
| 5,957,363 A | 9/1999 | Heck |
| 5,993,447 A | 11/1999 | Blewett et al. |
| 6,007,522 A | 12/1999 | Agro et al. |
| 6,007,544 A | 12/1999 | Kim |
| 6,015,431 A | 1/2000 | Thornton et al. |
| 6,017,352 A | 1/2000 | Nash et al. |
| 6,022,359 A | 2/2000 | Frantzen |
| 6,036,698 A | 3/2000 | Fawzi et al. |
| 6,063,113 A | 5/2000 | Kavteladze et al. |
| 6,074,416 A | 6/2000 | Berg et al. |
| 6,080,174 A | 6/2000 | Dubrul et al. |
| 6,099,547 A | 8/2000 | Gellman et al. |
| 6,113,609 A | 9/2000 | Adams |
| 6,113,611 A | 9/2000 | Allen et al. |
| 6,152,144 A | 11/2000 | Lesh et al. |
| 6,190,353 B1 | 2/2001 | Makower et al. |

(56) References Cited

U.S. PATENT DOCUMENTS

| | | |
|---|---|---|
| 6,214,029 B1 | 4/2001 | Thill et al. |
| 6,228,039 B1 | 5/2001 | Binmoeller |
| 6,231,515 B1 | 5/2001 | Moore et al. |
| 6,231,587 B1 | 5/2001 | Makower |
| 6,241,757 B1 | 6/2001 | An et al. |
| 6,241,758 B1 | 6/2001 | Cox |
| 6,251,084 B1 | 6/2001 | Coelho |
| 6,258,108 B1 | 7/2001 | Lary |
| 6,264,675 B1 | 7/2001 | Brotz |
| 6,290,485 B1 | 9/2001 | Wang |
| 6,309,415 B1 | 10/2001 | Pulnev et al. |
| 6,315,708 B1 | 11/2001 | Salmon et al. |
| 6,319,272 B1 | 11/2001 | Brenneman et al. |
| 6,322,495 B1 | 11/2001 | Snow et al. |
| 6,325,798 B1 | 12/2001 | Edwards et al. |
| 6,334,446 B1 | 1/2002 | Beyar |
| 6,348,064 B1 | 2/2002 | Kanner |
| 6,358,264 B2 | 3/2002 | Banko |
| 6,371,964 B1 | 4/2002 | Vargas et al. |
| 6,371,965 B2 | 4/2002 | Gifford et al. |
| 6,391,036 B1 | 5/2002 | Berg et al. |
| 6,402,770 B1 | 6/2002 | Jessen |
| 6,432,040 B1 | 8/2002 | Meah |
| 6,436,119 B1 | 8/2002 | Erb et al. |
| 6,447,524 B1 | 9/2002 | Knodel et al. |
| 6,447,533 B1 | 9/2002 | Adams |
| 6,451,042 B1 | 9/2002 | Bonutti |
| 6,454,765 B1 | 9/2002 | Leveen et al. |
| 6,475,168 B1 | 11/2002 | Pugsley et al. |
| 6,475,185 B1 | 11/2002 | Rauker et al. |
| 6,475,222 B1 | 11/2002 | Berg et al. |
| 6,485,496 B1 | 11/2002 | Suyker et al. |
| 6,488,653 B1 | 12/2002 | Lombardo |
| 6,494,888 B1 | 12/2002 | Laufer et al. |
| 6,503,247 B2 | 1/2003 | Swartz et al. |
| 6,508,252 B1 | 1/2003 | Berg et al. |
| 6,520,908 B1 | 2/2003 | Ikeda et al. |
| 6,535,764 B2 | 3/2003 | Imran et al. |
| 6,547,776 B1 | 4/2003 | Gaiser et al. |
| 6,575,967 B1 | 6/2003 | Leveen et al. |
| 6,610,100 B2 | 8/2003 | Phelps et al. |
| 6,614,595 B2 | 9/2003 | Igarashi |
| 6,616,675 B1 | 9/2003 | Evard et al. |
| 6,620,122 B2 | 9/2003 | Stinson et al. |
| 6,626,917 B1 | 9/2003 | Craig |
| 6,626,919 B1 | 9/2003 | Swanstrom |
| 6,632,197 B2 | 10/2003 | Lyon |
| 6,635,068 B1 | 10/2003 | Dubrul et al. |
| 6,638,213 B2 | 10/2003 | Ogura et al. |
| 6,645,205 B2 | 11/2003 | Ginn |
| 6,656,182 B1 | 12/2003 | Hayhurst |
| 6,656,206 B2 | 12/2003 | Corcoran et al. |
| 6,669,708 B1 | 12/2003 | Nissenbaum et al. |
| 6,682,536 B2 | 1/2004 | Vardi et al. |
| 6,699,277 B1 | 3/2004 | Freidberg et al. |
| 6,719,781 B1 | 4/2004 | Kim |
| 6,736,828 B1 | 5/2004 | Adams et al. |
| 6,746,472 B2 | 6/2004 | Frazier et al. |
| 6,746,489 B2 | 6/2004 | Dua et al. |
| 6,749,621 B2 | 6/2004 | Pantages et al. |
| 6,773,440 B2 | 8/2004 | Gannoe et al. |
| 6,835,189 B2 | 12/2004 | Musbach et al. |
| 6,846,323 B2 | 1/2005 | Yip et al. |
| 6,902,535 B2 | 6/2005 | Eberhart et al. |
| 6,916,332 B2 | 7/2005 | Adams |
| 6,921,361 B2 | 7/2005 | Suzuki et al. |
| 6,921,387 B2 | 7/2005 | Camrud |
| 6,942,678 B2 | 9/2005 | Bonnette et al. |
| 6,960,233 B1 | 11/2005 | Berg et al. |
| 6,966,917 B1 | 11/2005 | Suyker et al. |
| 6,974,467 B1 | 12/2005 | Gonzales, Jr. |
| 6,979,290 B2 | 12/2005 | Mourlas et al. |
| 7,018,401 B1 | 3/2006 | Hyodoh et al. |
| 7,022,131 B2 | 4/2006 | Derowe et al. |
| 7,056,325 B1 | 6/2006 | Makower et al. |
| 7,074,229 B2 | 7/2006 | Adams et al. |
| 7,077,850 B2 | 7/2006 | Kortenbach |
| 7,125,413 B2 | 10/2006 | Grigoryants et al. |
| 7,131,948 B2 | 11/2006 | Yock |
| 7,134,438 B2 | 11/2006 | Makower et al. |
| 7,150,723 B2 | 12/2006 | Meguro et al. |
| 7,153,314 B2 | 12/2006 | Laufer et al. |
| 7,156,857 B2 | 1/2007 | Pasricha et al. |
| 7,169,161 B2 | 1/2007 | Bonnette et al. |
| 7,175,646 B2 | 2/2007 | Brenneman et al. |
| 7,182,771 B1 | 2/2007 | Houser et al. |
| 7,204,842 B2 | 4/2007 | Geitz |
| 7,273,451 B2 | 9/2007 | Sekine et al. |
| 7,303,531 B2 | 12/2007 | Lee et al. |
| 7,309,341 B2 | 12/2007 | Ortiz et al. |
| 7,361,180 B2 | 4/2008 | Saadat et al. |
| 7,377,897 B1 | 5/2008 | Kunkel et al. |
| 7,390,323 B2 | 6/2008 | Jang |
| 7,416,554 B2 | 8/2008 | Lam et al. |
| 7,429,264 B2 | 9/2008 | Melkent et al. |
| 7,534,247 B2 | 5/2009 | Ortiz |
| 7,591,828 B2 | 9/2009 | Ortiz |
| 7,614,999 B2 | 11/2009 | Gellman et al. |
| 7,628,768 B2 | 12/2009 | Faul et al. |
| 7,637,919 B2 | 12/2009 | Ishikawa et al. |
| 7,731,693 B2 | 6/2010 | Melsheimer |
| 7,753,872 B2 | 7/2010 | Cragg et al. |
| 7,758,565 B2 | 7/2010 | Melsheimer |
| 7,785,275 B2 | 8/2010 | Melsheimer |
| 7,828,814 B2 | 11/2010 | Brenneman et al. |
| 7,845,536 B2 | 12/2010 | Mola et al. |
| 7,914,552 B2 | 3/2011 | Shelton, IV |
| 7,942,890 B2 | 5/2011 | D'Agostino et al. |
| 7,998,155 B2 | 8/2011 | Manzo |
| 8,016,782 B2 | 9/2011 | Brenneman et al. |
| 8,034,063 B2 | 10/2011 | Binmoeller |
| 8,088,171 B2 | 1/2012 | Brenneman |
| 8,187,289 B2 | 5/2012 | Tacchino et al. |
| 8,226,592 B2 | 7/2012 | Brenneman et al. |
| 8,236,014 B2 | 8/2012 | Brenneman et al. |
| 8,328,837 B2 | 12/2012 | Binmoeller |
| 8,357,193 B2 | 1/2013 | Phan et al. |
| 8,425,539 B2 | 4/2013 | Binmoeller et al. |
| 8,454,632 B2 | 6/2013 | Binmoeller et al. |
| 9,381,041 B2 | 7/2016 | Brown et al. |
| 9,888,926 B2 | 2/2018 | Phan et al. |
| 10,076,330 B2 | 9/2018 | Sander et al. |
| 10,952,732 B2 | 3/2021 | Binmoeller et al. |
| 2001/0004699 A1 | 6/2001 | Gittings et al. |
| 2001/0011170 A1 | 8/2001 | Davison et al. |
| 2001/0051809 A1 | 12/2001 | Houser et al. |
| 2002/0002401 A1 | 1/2002 | McGuckin et al. |
| 2002/0004663 A1 | 1/2002 | Gittings et al. |
| 2002/0019580 A1 | 2/2002 | Lau et al. |
| 2002/0042564 A1 | 4/2002 | Cooper et al. |
| 2002/0058897 A1 | 5/2002 | Renati |
| 2002/0058955 A1 | 5/2002 | Blatter et al. |
| 2002/0082627 A1* | 6/2002 | Berg ............... A61F 2/064 606/155 |
| 2002/0087176 A1 | 7/2002 | Greenhalgh |
| 2002/0138098 A1 | 9/2002 | Black et al. |
| 2002/0161341 A1 | 10/2002 | Stinson et al. |
| 2002/0183787 A1 | 12/2002 | Wahr et al. |
| 2002/0188301 A1 | 12/2002 | Dallara et al. |
| 2003/0014063 A1 | 1/2003 | Houser et al. |
| 2003/0032975 A1 | 2/2003 | Bonutti |
| 2003/0040803 A1 | 2/2003 | Rioux et al. |
| 2003/0045893 A1 | 3/2003 | Ginn |
| 2003/0050665 A1 | 3/2003 | Ginn |
| 2003/0069533 A1 | 4/2003 | Kakutani et al. |
| 2003/0073979 A1 | 4/2003 | Naimark et al. |
| 2003/0078604 A1 | 4/2003 | Walshe |
| 2003/0088256 A1 | 5/2003 | Conston et al. |
| 2003/0093118 A1 | 5/2003 | Ho et al. |
| 2003/0109900 A1 | 6/2003 | Martinek |
| 2003/0120292 A1 | 6/2003 | Park et al. |
| 2003/0163017 A1 | 8/2003 | Tam et al. |
| 2003/0195458 A1 | 10/2003 | Phelps et al. |
| 2003/0199991 A1 | 10/2003 | Stack et al. |

(56) References Cited

U.S. PATENT DOCUMENTS

| | | |
|---|---|---|
| 2003/0216749 A1 | 11/2003 | Ishikawa et al. |
| 2003/0236536 A1 | 12/2003 | Grigoryants et al. |
| 2004/0019322 A1 | 1/2004 | Hoffmann |
| 2004/0034371 A1 | 2/2004 | Lehman et al. |
| 2004/0044364 A1 | 3/2004 | Devries et al. |
| 2004/0049157 A1 | 3/2004 | Plishka et al. |
| 2004/0073108 A1 | 4/2004 | Saeed et al. |
| 2004/0122456 A1 | 6/2004 | Saadat et al. |
| 2004/0199087 A1 | 10/2004 | Swain et al. |
| 2004/0215220 A1 | 10/2004 | Dolan et al. |
| 2004/0230190 A1 | 11/2004 | Dahla et al. |
| 2004/0236346 A1 | 11/2004 | Parker |
| 2004/0243122 A1 | 12/2004 | Auth et al. |
| 2004/0249985 A1 | 12/2004 | Mori et al. |
| 2004/0260332 A1 | 12/2004 | Dubrul et al. |
| 2005/0022843 A1 | 2/2005 | Policicchio et al. |
| 2005/0033327 A1 | 2/2005 | Gainor et al. |
| 2005/0043781 A1 | 2/2005 | Foley |
| 2005/0049675 A1 | 3/2005 | Wallace |
| 2005/0059890 A1 | 3/2005 | Deal et al. |
| 2005/0059990 A1 | 3/2005 | Ayala et al. |
| 2005/0075654 A1 | 4/2005 | Kelleher |
| 2005/0080444 A1 | 4/2005 | Kraemer et al. |
| 2005/0096685 A1 | 5/2005 | Murphy et al. |
| 2005/0113868 A1 | 5/2005 | Devellian et al. |
| 2005/0120292 A1 | 6/2005 | Suzuki |
| 2005/0187567 A1 | 8/2005 | Baker et al. |
| 2005/0203344 A1 | 9/2005 | Orban et al. |
| 2005/0228413 A1 | 10/2005 | Binmoeller et al. |
| 2005/0251159 A1 | 11/2005 | Ewers et al. |
| 2005/0251208 A1 | 11/2005 | Elmer et al. |
| 2005/0277965 A1 | 12/2005 | Brenneman et al. |
| 2005/0277981 A1 | 12/2005 | Maahs et al. |
| 2006/0015006 A1 | 1/2006 | Laurence et al. |
| 2006/0047337 A1 | 3/2006 | Brenneman |
| 2006/0062996 A1 | 3/2006 | Chien et al. |
| 2006/0111672 A1 | 5/2006 | Seward |
| 2006/0111704 A1 | 5/2006 | Brenneman et al. |
| 2006/0116697 A1 | 6/2006 | Carter et al. |
| 2006/0142703 A1 | 6/2006 | Carter et al. |
| 2006/0142790 A1 | 6/2006 | Gertner |
| 2006/0167482 A1 | 7/2006 | Swain et al. |
| 2006/0184187 A1 | 8/2006 | Surti |
| 2006/0190021 A1 | 8/2006 | Hausman et al. |
| 2006/0190075 A1 | 8/2006 | Jordan et al. |
| 2006/0200177 A1 | 9/2006 | Manzo |
| 2006/0210605 A1 | 9/2006 | Chang et al. |
| 2006/0217748 A1 | 9/2006 | Ortiz |
| 2006/0217762 A1 | 9/2006 | Maahs et al. |
| 2006/0224183 A1 | 10/2006 | Freudenthal |
| 2006/0253088 A1 | 11/2006 | Chow et al. |
| 2006/0259051 A1 | 11/2006 | Nissl |
| 2006/0259074 A1 | 11/2006 | Kelleher et al. |
| 2006/0282087 A1 | 12/2006 | Binmoeller |
| 2007/0027534 A1 | 2/2007 | Bergheim et al. |
| 2007/0066863 A1 | 3/2007 | Rafiee et al. |
| 2007/0112363 A1 | 5/2007 | Adams |
| 2007/0112380 A1 | 5/2007 | Figulla et al. |
| 2007/0112383 A1 | 5/2007 | Conlon et al. |
| 2007/0123840 A1 | 5/2007 | Cox |
| 2007/0123917 A1 | 5/2007 | Ortiz et al. |
| 2007/0123934 A1 | 5/2007 | Whisenant et al. |
| 2007/0135825 A1 | 6/2007 | Binmoeller |
| 2007/0179426 A1 | 8/2007 | Selden |
| 2007/0197862 A1 | 8/2007 | Deviere et al. |
| 2007/0213812 A1 | 9/2007 | Webler et al. |
| 2007/0260273 A1 | 11/2007 | Cropper et al. |
| 2007/0265656 A1 | 11/2007 | Amplatz et al. |
| 2007/0270751 A1 | 11/2007 | Stangenes et al. |
| 2008/0009888 A1 | 1/2008 | Ewers et al. |
| 2008/0045989 A1 | 2/2008 | Welborn |
| 2008/0065012 A1 | 3/2008 | Hebert et al. |
| 2008/0071301 A1 | 3/2008 | Matsuura et al. |
| 2008/0077180 A1 | 3/2008 | Kladakis et al. |
| 2008/0140172 A1 | 6/2008 | Carpenter et al. |
| 2008/0154153 A1 | 6/2008 | Heuser |
| 2008/0161645 A1 | 7/2008 | Goldwasser et al. |
| 2008/0167524 A1 | 7/2008 | Goldwasser et al. |
| 2008/0171944 A1 | 7/2008 | Brenneman et al. |
| 2008/0183080 A1 | 7/2008 | Abraham |
| 2008/0215089 A1 | 9/2008 | Williams et al. |
| 2008/0243151 A1 | 10/2008 | Binmoeller et al. |
| 2008/0249481 A1 | 10/2008 | Crainich et al. |
| 2008/0249562 A1 | 10/2008 | Cahill |
| 2008/0262518 A1 | 10/2008 | Freudenthal |
| 2009/0024149 A1 | 1/2009 | Saeed et al. |
| 2009/0030380 A1 | 1/2009 | Binmoeller |
| 2009/0062841 A1 | 3/2009 | Amplatz et al. |
| 2009/0082803 A1 | 3/2009 | Adams et al. |
| 2009/0138071 A1 | 5/2009 | Cheng et al. |
| 2009/0143713 A1 | 6/2009 | Van et al. |
| 2009/0143759 A1 | 6/2009 | Van et al. |
| 2009/0143760 A1 | 6/2009 | Van et al. |
| 2009/0177264 A1 | 7/2009 | Ravenscroft |
| 2009/0177288 A1 | 7/2009 | Wallsten |
| 2009/0227835 A1 | 9/2009 | Terliuc |
| 2009/0259288 A1 | 10/2009 | Wijay et al. |
| 2009/0281379 A1 | 11/2009 | Binmoeller et al. |
| 2009/0281557 A1 | 11/2009 | Sander et al. |
| 2010/0099947 A1 | 4/2010 | Sato et al. |
| 2010/0105983 A1 | 4/2010 | Oneda et al. |
| 2010/0130993 A1 | 5/2010 | Paz et al. |
| 2010/0191167 A1 | 7/2010 | Laufer |
| 2010/0261962 A1 | 10/2010 | Friedberg |
| 2010/0268029 A1 | 10/2010 | Phan et al. |
| 2010/0268175 A1 | 10/2010 | Lunsford et al. |
| 2010/0268316 A1 | 10/2010 | Brenneman et al. |
| 2011/0112622 A1 | 5/2011 | Phan et al. |
| 2011/0137394 A1 | 6/2011 | Lunsford et al. |
| 2012/0109277 A1 | 5/2012 | Lepulu et al. |
| 2012/0130417 A1 | 5/2012 | Lepulu et al. |
| 2012/0136426 A1 | 5/2012 | Phan et al. |
| 2014/0330294 A1 | 11/2014 | Binmoeller et al. |

FOREIGN PATENT DOCUMENTS

| | | |
|---|---|---|
| CA | 2482697 A1 | 3/2005 |
| DE | 102006050385 A1 | 4/2008 |
| EP | 0637431 A1 | 2/1995 |
| EP | 0794734 B1 | 8/2002 |
| EP | 1314404 A2 | 5/2003 |
| EP | 1520526 A1 | 4/2005 |
| EP | 1520532 A2 | 4/2005 |
| EP | 0959777 B1 | 7/2005 |
| EP | 1857135 A2 | 11/2007 |
| EP | 1894514 A2 | 3/2008 |
| EP | 1908421 A1 | 4/2008 |
| EP | 1331885 B1 | 3/2009 |
| EP | 1824404 B1 | 8/2012 |
| GB | 2020557 A | 11/1979 |
| JP | S58-35219 A | 3/1983 |
| JP | S62-233168 A | 10/1987 |
| JP | H05-137794 A | 6/1993 |
| JP | H05-192407 A | 8/1993 |
| JP | H05-329165 A | 12/1993 |
| JP | H05-508563 A | 12/1993 |
| JP | H07-096038 A | 4/1995 |
| JP | H08-071158 A | 3/1996 |
| JP | H08-504940 A | 5/1996 |
| JP | H08-509639 A | 10/1996 |
| JP | H08-299455 A | 11/1996 |
| JP | H09-500047 A | 1/1997 |
| JP | H09-504186 A | 4/1997 |
| JP | H09-140804 A | 6/1997 |
| JP | H10-094543 A | 4/1998 |
| JP | H10-155799 A | 6/1998 |
| JP | H11-512318 A | 10/1999 |
| JP | 2000-500045 A | 1/2000 |
| JP | 2000-237303 A | 9/2000 |
| JP | 2001-503657 A | 3/2001 |
| JP | 2001-511658 A | 8/2001 |
| JP | 2001-275947 A | 10/2001 |
| JP | 2001-517524 A | 10/2001 |
| JP | 2002-119516 A | 4/2002 |

(56) References Cited

FOREIGN PATENT DOCUMENTS

| JP | 2002-524196 A | 8/2002 |
|---|---|---|
| JP | 2002-534208 A | 10/2002 |
| JP | 2003-526448 A | 9/2003 |
| JP | 2004-512153 A | 4/2004 |
| JP | 2004-216192 A | 8/2004 |
| JP | 2005-525865 A | 9/2005 |
| JP | 2007-514462 A | 6/2007 |
| JP | 2008-534029 A | 8/2008 |
| JP | 2009-500051 A | 1/2009 |
| WO | 97/27898 A1 | 8/1997 |
| WO | 99/23952 A1 | 5/1999 |
| WO | 00/24449 A1 | 5/2000 |
| WO | 00/72909 A1 | 12/2000 |
| WO | 01/21247 A1 | 3/2001 |
| WO | 01/72367 A1 | 10/2001 |
| WO | 02/87469 A2 | 11/2002 |
| WO | 03/20106 A2 | 3/2003 |
| WO | 03/24305 A2 | 3/2003 |
| WO | 03/71962 A2 | 9/2003 |
| WO | 2004/087236 A2 | 10/2004 |
| WO | 2005/011463 A2 | 2/2005 |
| WO | 2005/096953 A1 | 10/2005 |
| WO | 2006/115811 A1 | 11/2006 |
| WO | 2007/047151 A1 | 4/2007 |
| WO | 2007/115117 A1 | 10/2007 |
| WO | 2008/005510 A2 | 1/2008 |
| WO | 2008/005888 A2 | 1/2008 |
| WO | 2008/040573 A1 | 4/2008 |

OTHER PUBLICATIONS

Binmoeller et al.; Silicone-covered expanadable metallic stents in the esophagus: an experimental study; Endoscopy; 24; pp. 416-420; Jun. 1992.

Maisin et al: "Patency of Endoscopic Cystoduodenostomy Maintained by a Z Stent," Gastrointestinal Endoscopy; 40 6); pp. 765-768; Nov. 1994.

Kwan et al., EUS-guided cholecystenterostomy: a new technique, Gastrointestinal Endoscopy, 66(3), pp. 582-586, Sep. 2007.

Blum et al., Endoluminal stent-grafts for infrarenal abdominal aortic aneurysms, NEJM, 336(1), pp. 13-20, Jan. 2, 2996.

Spillner er et al.; Initial clainical experiences with endovascular stent-grafts for treatment of infrarenal abdominal aortic aneurysm (in German w/ English Summary); Zentralbl Chir.; 121(9); pp. 727-733; 1996 (year of pub. sufficiently earlier than effective US filed and any foreign priority date).

Chopita et al., Endoscopic gastroenteric anastomlosis using magnets, Endoscopy, vol. 37, No. 4, pp. 313-317, Apr. 2005.

Davies et al., Percutaneous cystogastrostomy with a new catheter for drainage of pancreatic pseudocysts and fluid Collections, Cardiovascular and Interventional Radiology, 19, pp. 128-131, Mar. 1996.

Schaer et al., Treatment of malignant esophageal obstruction with silicon-coated metallic self-expanding stents, Gastrointestinal Endoscopy, 38(1), pp. 7-11, Jan. 1992.

European Office Action dated Aug. 7, 2009 for EP 05732207.5.

European Search Report and Search Opinion dated Jul. 19, 2011 for EP 08836744.6.

European Search Report dated Jun. 3, 2009 for EP 05732207.5.

European Search Report for Application No. 18165477.3, dated Jul. 30, 2019, 7 pages.

Fritscher-Ravens et al., A through-the-scope device for suturing and tissue approximation under EUS control, Gastro Endo, 56(5), pp. 737-742, Nov. 2002.

Fritscher-Ravens et al., Transgastric gastropexy and hiatal hernia repair for GERO under EUS control, A porcine model, Castro Endo, 59(1), pp. 89-85, Jan. 2004.

International search report and written opinion dated Dec. 1, 2008 for PCT/US2008/078477.

International Search Report and Written Opinion received for PCT Patent Application No. PCT/US2005/011921, mailed on Dec. 6, 2006, 05 pages.

Kahaleh et al; Interventional EUS Guided Cholangiography: Evaluation of a Technique in Evolution; check.

* cited by examiner

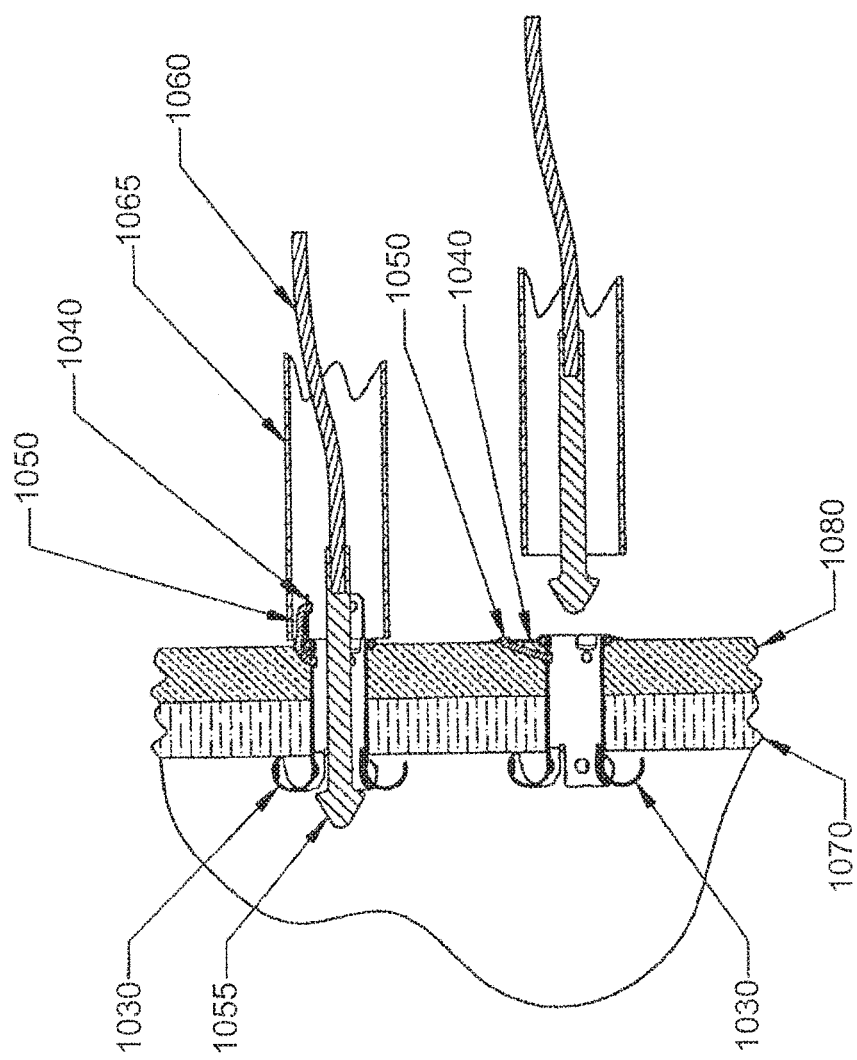

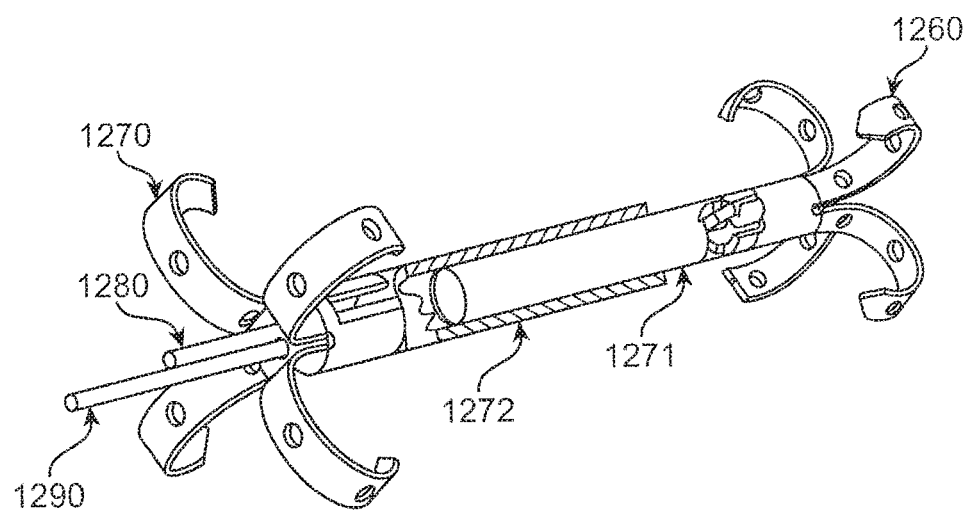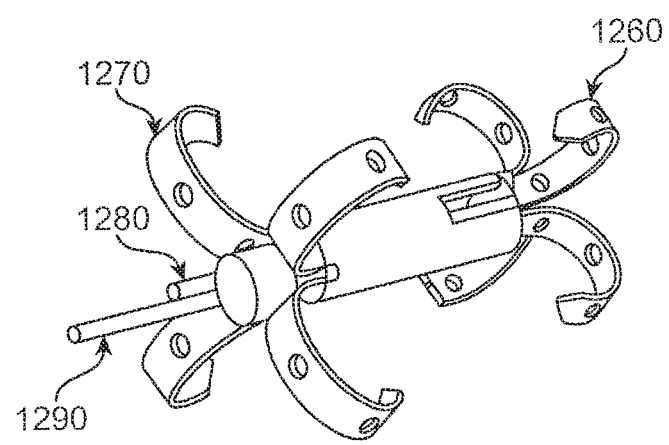
FIG. 27

LUMINAL STRUCTURE ANCHORING DEVICES AND METHODS

CROSS REFERENCE TO RELATED APPLICATIONS

This application is a continuation of U.S. application Ser. No. 17/412,385, filed on Aug. 26, 2021, which is a continuation of U.S. application Ser. No. 15/331,151, filed on Oct. 21, 2016, which is a continuation of is a continuation of U.S. application Ser. No. 13/865,098, filed on Apr. 17, 2013, which is a continuation of is a continuation of U.S. application Ser. No. 11/867,636 filed on Oct. 4, 2007, entitled "Luminal Structure Anchoring Devices and Methods", and issued as U.S. Pat. No. 8,425,539 on Apr. 23, 2013, which is a continuation-in-part (CIP) of U.S. application Ser. No. 10/822,138, filed Apr. 12, 2004, entitled "Automated Transluminal Targeting Device and Anchoring Devices and Methods", the disclosures of which are hereby expressly incorporated by reference.

FIELD

The invention relates to a device for endoscopy or endosonography-guided transluminal interventions whereby an anastomosis can be formed between two luminal structures in the body. More specifically devices and methods are described to anchor, create a fluid conduit and to approximate luminal structures using an expandable hollow stent.

BACKGROUND

Endoscopy and endosonography-guided interventions have certain advantages over alternative surgical and percutaneous-guided procedures. Interventions that employ endoscopy or endosonography may avoid some of the harmful effects of alternative procedures. One technique that has been explained is a technique for endoscopy and endosonography-guided biopsy. Such a technique and associated devices are described, for example, in U.S. Pat. No. 6,228,039, which is hereby expressly incorporated by reference. A need exists, however, for other diagnostic and therapeutic interventional applications and related devices that may be performed in an endoscopy or endosonography-guided environment.

In particular, a need exists for such devices and techniques that can traverse a first layer of tissue, such as the wall of the bowel, bladder, or other organ or structure that can be accessed endoscopically, and penetrate into or through another layer of tissue such as the wall of a hollow or solid organ, hollow body, luminal structure, duct, vessel, or soft tissue structure, such as a muscle or ligament. In certain surgical operations, for example, a need exists to be able to connect and create an artificial lumen (anastomosis) between two neighboring luminal structures, such as, for example, two segments of bowel. Sometimes the need exists to approximate the two luminal structures before or simultaneous to the creation of an artificial lumen or connecting conduit.

Further, a need exists in certain surgical procedures to attach or affix two neighboring structures, such as the stomach to the diaphragm (gastroplexy) or the bladder to the abdominal wall (cystoplexy). Additionally, a need exists to be able to connect a first portion of the stomach with a second portion of the stomach (stomach stapling). A need also exists to be able to affix diagnostic and therapeutic devices to an organ or tissue. For example, a need exists to be able to implant a gastric pacemaker to treat gastroparesis. Furthermore, a need exists to perform the functions described above in a manner that is automated. For example, in circumstances in which it is desired that an operation take place from within a luminal structure, a surgeon may have limited ability to manipulate a needle, anchor, or other penetrating device to perform procedures such as those listed above, and in particular to position tissue or to create an artificial lumen. Thus, a need exists for an appropriate automatic tissue targeting device.

Furthermore the need exists to connect, approximate and create an artificial lumen (anastomosis) between two neighboring luminal structures. Such an artificial lumen preferably has a large diameter. A large diameter artificial lumen or conduit may facilitate fluid exchange between the luminal structures, the insertion of instruments or the removal of body tissues such as gall stones from one structure to another.

SUMMARY OF THE DISCLOSURE

The present invention relates . . . . The present invention may solve the needs in the art stated above and may provide certain advantages over the prior art. The present invention solves the need for the ability to perform additional techniques by providing an apparatus capable of use in such techniques.

One embodiment of the present invention may be an apparatus including a roughly hollow cylindrical central member having a proximal end and a distal end; a leg member, attached to a distal end of the central member, wherein at least a portion of the leg member is adapted to permit production of an expanded distal radius in the apparatus; a tether attached to a proximal portion of the central member; an expander member, a distal portion of which is aligned co-axially through the central member; and a pusher member aligned co-axially around a proximal portion of the expander member and adapted to prevent the movement in a proximal direction of the central member.

In an embodiment employing a cylindrical central member, there may be a number of leg members. These leg members may, for example, be segments of the cylinder. In an embodiment shown in FIG. 4, for example, the leg members are shown curled back, but it may be apparent from that figure that the four legs are each roughly a quarter of the circumference of the cylinder. Of course, there is no requirement that the legs be implemented in such a manner or comprise such a circumference of the cylinder. For example, a cylindrical member may be used. Such a cylindrical member may be adapted to transform from an approximately cylindrical shape to an approximately conical or pyramidal shape. Some examples include a "leg" deployed like the canopy of an umbrella, or a "leg" deployed by removing a sheath from an elastic (when reference is made to elastic, reference to superelastic is included) member shaped somewhat like a shuttlecock Additionally, a multiplicity of legs, such as 2, 3, 4, or more legs may be used. Such legs may be malleable or elastic. An example material for use as an elastic material is a shape memory alloy such as Nitinol. Other structures that may be used as a leg include, for example, tines, fingers, or hooks. The deployment of legs may be described as an expanding process, or by other terms, such as an unfurling process.

In an embodiment that may be employed in the lumen of a tissue or organ, the distal end may refer to the end most outwardly radial. In general, the distal end refers to the end closest to the first layer of tissue prior to normal use.

Another embodiment of the present invention may be the apparatus described above, but further including a pre-biasing device adapted to selectively force at least a portion of the apparatus in a distal direction, and an outer sleeve surrounding the apparatus, wherein the outer sleeve is adapted to be fitted to an endoscope. The outer sleeve may be attached to the described apparatus directly or medially, or may be slidably positioned relative to the apparatus. The outer sleeve may aid the operator in directing the application of the apparatus to target tissue.

Another embodiment of the present invention may be the apparatus described above, but further including a pre-biasing device adapted to selectively force at least a portion of the apparatus in a distal direction, and an outer sleeve surrounding the apparatus, wherein the outer sleeve is adapted to be fitted to an endoscope. The outer sleeve may be attached to the described apparatus directly or medially, or may be slidably positioned relative to the apparatus. The outer sleeve may aid the operator in directing the application of the apparatus to target tissue.

Another embodiment of the present invention may be an apparatus including a roughly hollow cylindrical central member having a proximal end and a distal end; a leg member, attached to a distal end of the central member, wherein at least a portion of the leg member is adapted to permit production of an expanded distal radius in the apparatus; and a shoulder member attached to a proximal end of the central member, the shoulder member being adapted to limit movement of the central member in a distal direction. The shoulder member may be collapsible to allow deployment and may be configured to automatically and/or manually deploy.

Another embodiment of the present invention may be an apparatus including a roughly hollow cylindrical central member having a proximal end and a distal end, and a leg member, attached to a distal end of the central member, wherein at least a portion of the leg member is adapted to permit production of an expanded distal radius in the apparatus.

Another embodiment of the present invention may be an apparatus including a roughly hollow cylindrical central member having a proximal end and a distal end; a kg member, attached to a distal end of the central member, wherein at least a portion of the leg member is adapted to permit production of an expanded distal radius in the apparatus; and a tether attached to a proximal portion of the central member.

Another embodiment of the present invention may be methods of use, including anchoring a second tissue to a first luminal structure, wherein the second tissue is anchored by use of an expandable anchor that is adapted to perform the steps of penetrating through a first luminal structure, penetrating at least into a portion of a second tissue, and holding the second tissue in approximately constant position relative to at least a region of the first luminal structure. The step of holding the second tissue in approximately constant position relative to at least a region of the first luminal structure may be performed by an embodiment of the present invention including an anchor, without regard to the speed or precise manner by which the anchor is inserted.

In such a method of use, the second tissue may be a luminal structure. Moreover, these luminal structures may be a hollow organ such as a segment of the bowel (for example, esophagus, stomach, small intestine, and colon), bladder, gallbladder, uterus, or bronchotracheal tree. These luminal structures may also be ductal structures such as the bile duct, pancreatic duct, urethra, or ureter. These luminal structures may also be vascular structures such as an artery or a vein. The cylindrical central members described above may serve to create a conduit or anastomosis between two luminal structures.

One embodiment of the present invention may be an apparatus including a substantially hollow central member adapted to permit the passage of a penetrating member adapted to penetrate tissue and a first leg member connected to a distal portion of the central member, wherein the first leg member may be adapted to produce an increase in a distal radius of the apparatus and wherein the increase may be adapted to restrain motion of the apparatus in a proximal direction. An embodiment may, for example, be adapted such that the first leg member employs a technique for producing an increased radius such as by being self-expanding or by being manually expandable. In a particular embodiment, the first leg member may be adapted to expand in radius in response to the proximal motion of the penetrating member.

An embodiment may, for example, be fashioned with the first leg member including a shape memory alloy. Other parts of the embodiment may also include shape memory alloy, such as, for example, the hollow central member.

In a particular embodiment, the first leg member may include a first end connected to a distal portion, and a second end that extends approximately proximally prior to increasing the radius of the apparatus. The fast leg member may, for example, include a first end connected to a distal portion, and may also include a second end that extends approximately distally prior to increasing the radius of the apparatus.

In an embodiment of the present invention, the first leg member may be adapted to expand in radius in response to the proximal motion of an encompassing sheath. Such a sheath may be particularly valuable in an embodiment in which shape memory or a self-expanding mechanism is used to increase a distal, medial, or proximal radius of the device.

In a further embodiment of the present invention, the apparatus may also include a second leg member connected to a proximal portion of the central member, wherein the second leg member is adapted to produce an increase in the proximal radius of the apparatus and wherein the increase is adapted to restrain motion of the apparatus in a distal direction. Such an embodiment may be designed such that the second leg member is adapted to expand in radius in response to the proximal motion of an encompassing sheath. In a particular embodiment, the second leg member may be adapted to expand in radius by means of one or more rubber bands.

In a particular embodiment, the hollow central member may be adapted to be a stent, the stent having an inner lumen. This stent may be covered to facilitate the passage of fluid through the inner lumen of the stent. Furthermore, the central member may be adapted to be expandable in diameter so that exchange of fluids is enhanced or the introduction of various instruments is facilitated. Additionally, the central member may include a shape memory alloy mesh. Such a mesh may be an expandable mesh that is trained to an expanded diameter but restrained to a narrower diameter by a removable encompassing sheath.

A further embodiment of the present invention may also include a tab connected to the central member and directed radially inward. The tab may be adapted to translate force in an axial proximal direction into force in a radially outward direction.

A further embodiment of the present invention may include a method of forming a conduit between a distal and a proximal luminal structure including positioning a distal retention member in or near the distal luminal structure and positioning a proximal retention member in or near the proximal luminal structure. The distal and proximal retention members are coupled to a hollow central member. The method further may include drawing the distal and proximal retention members toward each other such that a portion of the luminal structures are brought into closer approximation than before the intervention and held in close approximation to each other. The method may further include expanding the distal retention member and/or expanding the proximal retention member so that these retention members may act as anchors to secure the luminal structures to the retention members.

A further embodiment of the present invention may include shortening the central member as part of the approximation method described. This may be facilitated by the application of an axial compression force on the central member such that the length of the central member is shortened and the diameter of the central member is expanded. The central member may also be a stent or mesh that is comprised of two concentric hollow sections that shorten by sliding one hollow section inside the other.

In one particular embodiment of the present invention the device may be removable from the body once the therapeutic need has been met. Furthermore the device may be reabsorbed by the body or in other words the device may be bioabsorbable.

It is understood that both the foregoing general description and the following detailed description are exemplary and explanatory only and are not restrictive of the invention as claimed. The accompanying drawings illustrating an embodiment of the invention and together with the description serve to explain the principles of the invention.

BRIEF DESCRIPTION OF THE DRAWINGS

FIGS. 17A and 178 are drawings of an embodiment of an anchor with a collapsible shoulder.

FIG. 18 is a two-step sectional view drawing of an embodiment of the collapsible shoulder anchor in use.

FIG. 27 is a perspective view of an anchor that can be shortened in length by sliding two members together.

DETAILED DESCRIPTION

Figure 1:
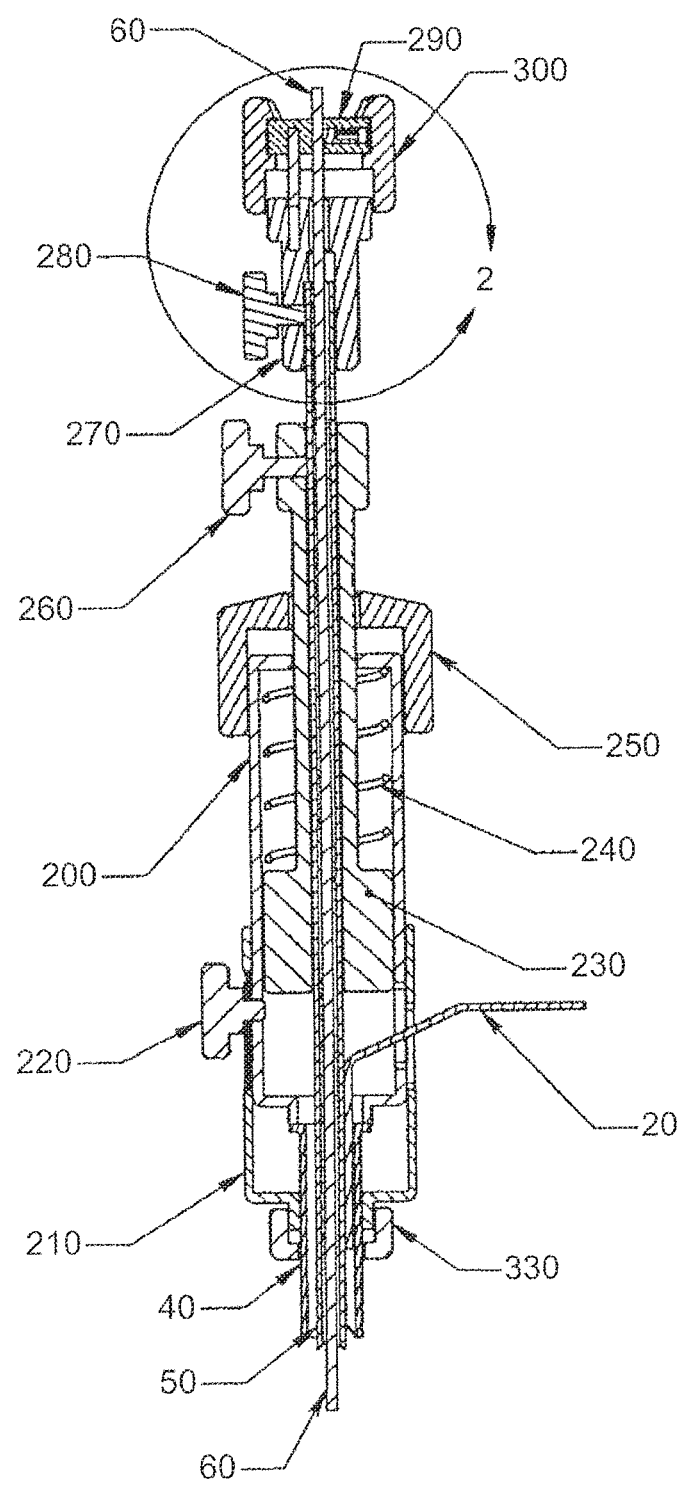
FIG. 1 is a drawing of an installation device for the anchors and other hardware of the present invention.

His to be understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a suture" is a reference to one or more sutures and includes equivalents thereof known to those skilled in the art. The materials that may be used in conjunction with the present invention may include conventional materials such as stainless steel, other surgical alloys of steel, various biocompatible plastics and elastomers, and other conventional materials. In general it may be valuable to avoid using materials that are likely to cause allergic reactions or inflammation, unless such a result is desired.

Reference herein to the term "endoscope" refers not only to conventional endoscopes, but also to any rigid, semi-rigid, or flexible optical instrument for use in visual examinations of the interior of the human body. Such examinations may include, for example, examinations of bodily canals or vessels such as blood vessels or hollow organs such as stomachs, intestines, colons, the heart or bladders. The term "endoscope" also includes angioscopes and also echo-endoscopes, which may include an ultrasound transducer at, for example, the tip of the device.

The present invention may be an embodiment that permits the automation of a tissue penetrating device by means of a pre-biasing device, which includes a member such as compressed gas compartment, a coil spring, or a torsion spring. In a specific embodiment, an integrated spring coil component, such as a compression spring component, may be used. Although a compression spring coil may be one component that may be used to forward-bias a portion of the device, other components may be used as well. For example, other types of elastically defined mechanical spring elements, compressed air, chemical combustion, or magnetic repulsion (or attraction) may also be used a pre-biasing device.

The compression spring, or other pre-biasing device, may be loaded. On release of the component, a tissue-penetrating component may shoot forward at high velocity. The velocity that may be desirable may depend on the tissue whose penetration is desired. A high velocity operation avoids striction effect and hence is more repeatable and accurate. Thus, the device may be able to penetrate in a more predictable and precisely calculable fashion. Further, the device may penetrate more than one tissue in a single forward movement or in more than one forward movement.

Thus, the device may be used to penetrate through the wall of a luminal structure into and through a wall of an adjacent luminal structure. Thereafter, the adjacent tissue may be engaged by an anchoring or connecting member. Thus, the device may be able to create an anastomotic connection between two luminal structures.

In certain embodiments, a device according to the present invention may be a tissue penetrating device that is inserted though the instrumentation channel of an endoscope, echo-endoscope, or the like. The handle of the device may be attached to the inlet port of the endoscope or echo-endoscope. Examples of such endoscopes are found, for example, in U.S. Pat. Nos. 6,638,213; 6,614,595; and 6,520,908. The tissue penetrating device may be manually advanced or retracted. Additionally, the forward-biasing device (for example, a compression spring) may be loaded and released. This may enable the tissue penetrating device to shoot forward with high velocity on the release of the device, which may occur via the release (or depression) of a trigger.

The tissue penetrating device may, for example, take the form of a barbed needle. The needle may be housed in a protective outer sheath. The outer sheath may serve to protect the instrumentation channel in the endoscope from the needle, as well as to protect the needle. The outer sheath may be adapted to be separate from the tissue penetrating device. Thus, the outer sheath may be moved independently of the tissue penetrating device. The outer sheath may further serve as a guide for the tissue penetrating device. Finally, the outer sheath may also serve to dilate or enlarge a tissue penetration tract. The handle of the device may be screwed and thereby securely anchored into the inlet port of the instrumentation channel of the endoscope using a Luer lock mechanism. This may be useful to prevent the handle from back-firing after the forward-biasing device is activated.

In the example of a spring-loaded embodiment, the distance of forward (or as it will be referred to herein, distal) movement of the tissue penetrating device may be controlled at the handle. For example, in one embodiment, the degree to which the spring is compressed or the degree to which the spring is permitted to travel may precisely control the distal movement of the tissue penetrating device. In an embodiment in which an anchor is to be inserted, the method of insertion is not essential to the operation of the anchor, although controlled, rapid insertion may accrue the benefits described.

Figure 2:
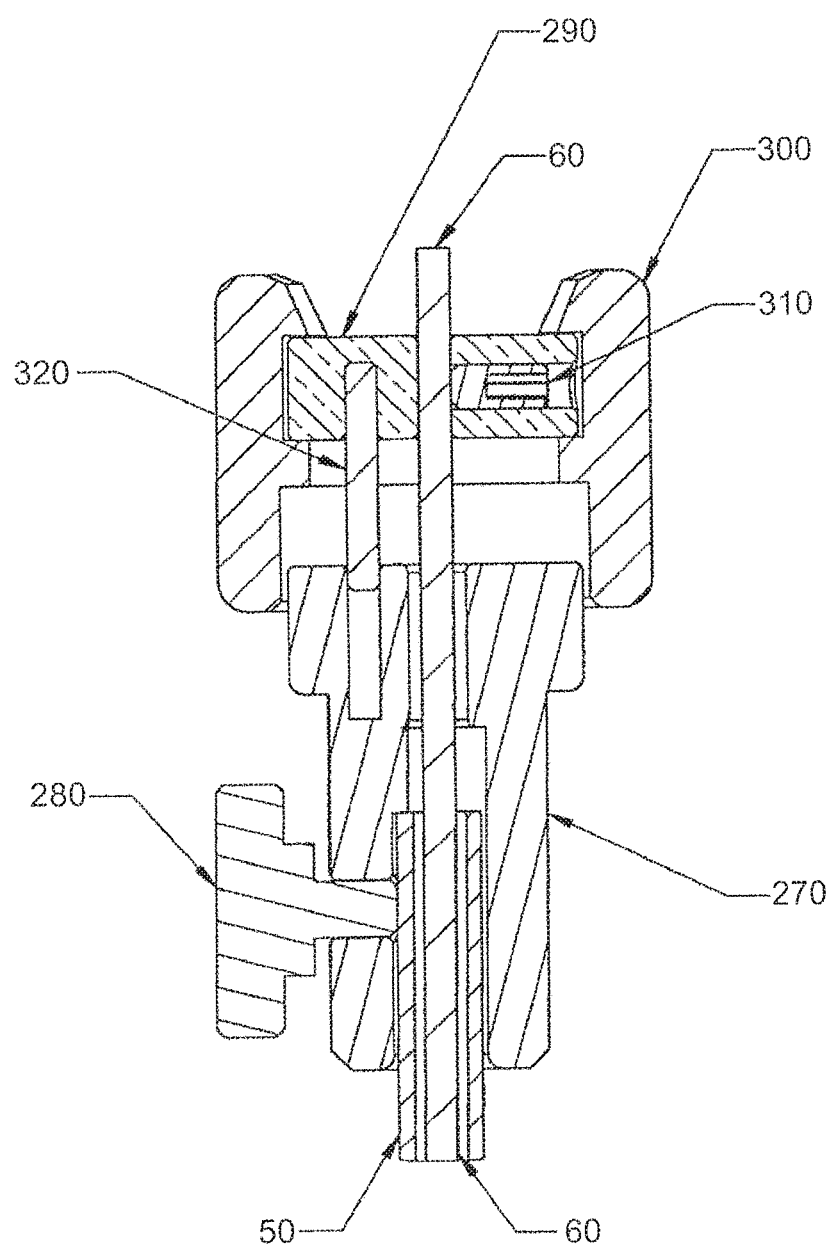
FIG. 2 is a detail drawing of a relevant portion of FIG. 1.

FIG. 1 depicts an installation device for the anchors and other hardware of the present invention, and may be an embodiment of the present invention. FIG. 2 is a detailed depiction of a portion 2 of FIG. 1. This installation device may, for example, be attached to an endoscope or echoendoscope. An example of such an attachment may be found in U.S. Pat. No. 6,228,039, which is hereby incorporated in its entirety herein by reference.

The embodiment depicted in FIGS. 1 and 2 may be assembled as follows. The activation cable assembly (including outer sheath 40, pusher 50, tether 60, and suture 20) may be threaded. The locknut 330 may be installed prior to threading. The locknut 330 may be used to assemble this embodiment together with an endoscope.

Next the suture 20 may be pushed through an opening that may be provided in main cylinder 200 and outer sleeve 210. Next, outer sleeve 210 may be attached to an endoscope via locknut 330 or via other appropriate attachment device. The outer sheath 40 may be attached onto the main cylinder 200 using an appropriate connection, such as a screw (not shown). Main cylinder 200 may be fastened to outer sleeve 210 by stop screw 220. The stop screw 220 may permit setting the relative position of main cylinder 200 and outer sleeve 210. One position that may be useful is one in which outer sheath 40 is consequently adjusted to an appropriate place within a patient. Sliding piston 230 may be tensioned and locked using pre-bias latch/release (not shown) as described in U.S. Pat. No. 6,228,039. It may be valuable to identify whether pusher 50 is in correct axial position along outer sheath 40. If not, it may be valuable to adjust the position of pusher 50 accordingly. Stop screw 260 may be used to lock pusher 50 in an appropriate position once adjusted. Calibration cap 250 may be turned on mating threads on main cylinder 200 to adjust the amount of travel upon the release of the compression spring 240. End cap 270 may be installed into the end of pusher 50. The end cap 270 may be pushed down until the end of its axial travel has been reached. The end cap 270 may then be fastened in place with a locking screw 280. This step of installation may be performed without damp nut 290 or expansion nut 300 in place.

Clamp nut 290 together with anti-rotation pin 320 and expansion nut 300 may be installed over the tether 60. In this embodiment, expansion nut 300 may snap over clamp nut 290 to form a subassembly. Expansion nut 300 may be screwed down the threads of end cap 270 until the shoulders contact It may be valuable to confirm that tether 60 is appropriately placed.

The locking screw 310 may then be tightened.

The device as described to this point may be used to deploy the anchor (not shown). After deploying the anchor, the expansion nut 300 may be rotated backwards until the proper expansion of the anchor (not shown) has been obtained. Expansion nut 300 may be connected to tether 60. Tether 60 may be connected to an expander. Turning expansion nut 300 creates relative motion between tether 60 and pusher 50.

Figure 3:
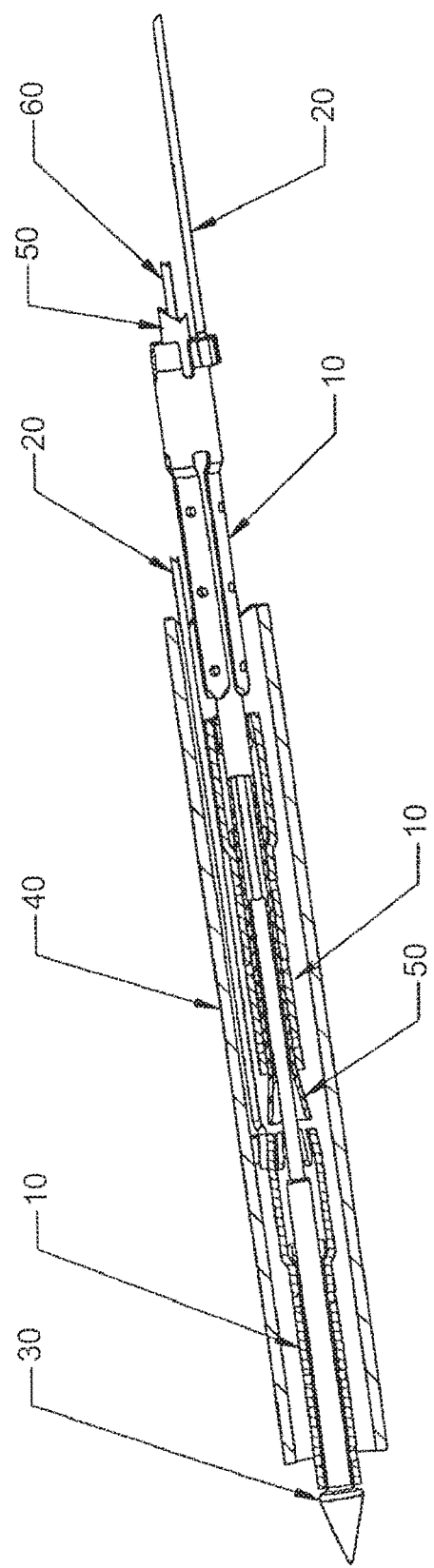
FIG. 3 is a sectional view of an embodiment of the present invention.

FIG. 3 depicts an embodiment of the present invention in a sectional view. This embodiment of the present invention may be inserted into tissue. This embodiment includes an expander 30 at a distal end of the apparatus, three anchors 10, a pusher 50, an outer sheath 40, sutures 20, and a tether 60. In this example, the expander 30 may be forced through a surface in a distal direction. The other elements depicted, except for the outer sheath, may also at least partially penetrate the surface. Thus, for example, one of the anchors 10 may partially penetrate the surface. A mechanism (not shown) may be used to retract the expander 30 in a proximal direction. The pusher 50 may prevent the anchor 10 from retracting in the proximal direction. As the expander 30 retracts, it may force the anchor 10 to expand. This expansion may result in anchor 10 having a greater diameter at its distal end. Thus the anchor 10 may be prevented from moving back through the surface in a proximal direction. However, a tether 60 may provide a tensile force in the proximal direction that may keep the anchor in contact with the penetrated surface. In certain circumstances, it may be advisable to apply an anchor 10 that has a suture 20 attached. Additionally, although this method may use motion of the expander, it may also use motion of the anchor relative to the expander.

Figure 4:
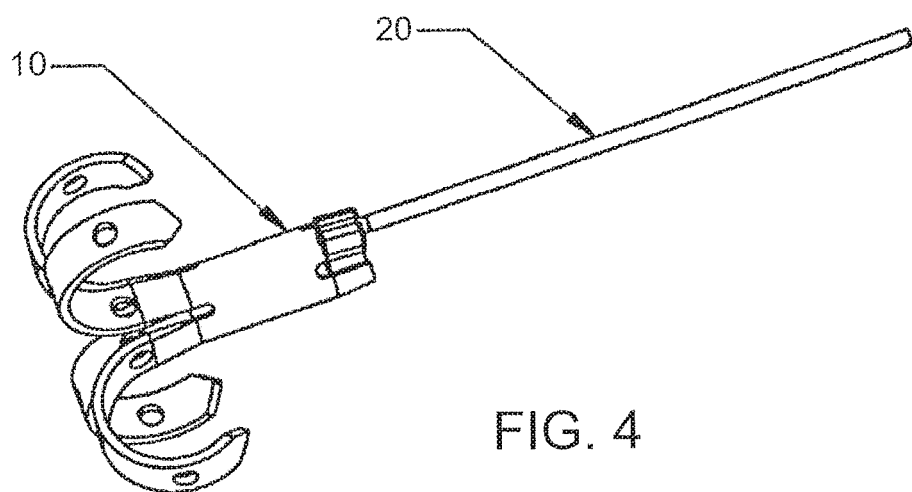
FIG. 4 is a perspective view drawing of an embodiment of the present invention that may be an anchor and may be, as shown, in an expanded state with leg members deployed.

FIG. 4 depicts an embodiment of the present invention that may be an anchor. This embodiment includes an expanded-form anchor 10 at a distal end and a suture 20 at a proximal end. As shown here, an anchor 10 may be expanded (shown already expanded), creating a distal region with an effective diameter larger than the hole occupied by the more proximal region. A suture 20 may be attached to the expanded anchor 10. The suture 20 may, in some embodiment be more easily attached prior to expansion of the anchor 10. In particular, it may be desirable to attach the suture before penetrating a surface with the anchor. FIG. 4 depicts an embodiment of the present invention that may be an anchor. This embodiment includes an expanded-form anchor 10 at a distal end and a suture 20 at a proximal end. As shown here, an anchor 10 may be expanded (shown already expanded), creating a distal region with an effective diameter larger than the hole occupied by the more proximal region. A suture 20 may be attached to the expanded anchor 10. The suture 20 may, in some embodiments be more easily attached prior to expansion of the anchor 10. In particular, it may be desirable to attach the suture before penetrating a surface with the anchor.

Figure 5:
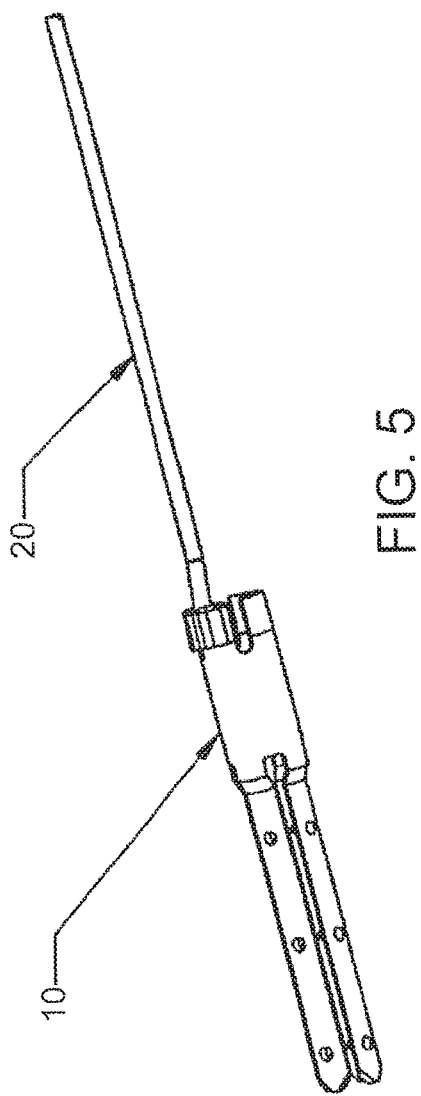
FIG. 5 is another perspective view drawing of an embodiment of the present invention that may be an anchor and may be, as shown, in an unexpanded state

FIG. 5 depicts another embodiment of the present invention that may be an anchor. This embodiment includes an anchor 10 at a distal end and a suture 20 at a proximal end. As shown, the anchor 10 may be in a pre-expansion form. Such a form may be useful, for example, in aiding in the insertion of an anchor through a surface. As shown here, a suture 20 may be attached to the anchor 10 prior to expansion.

Figure 6:
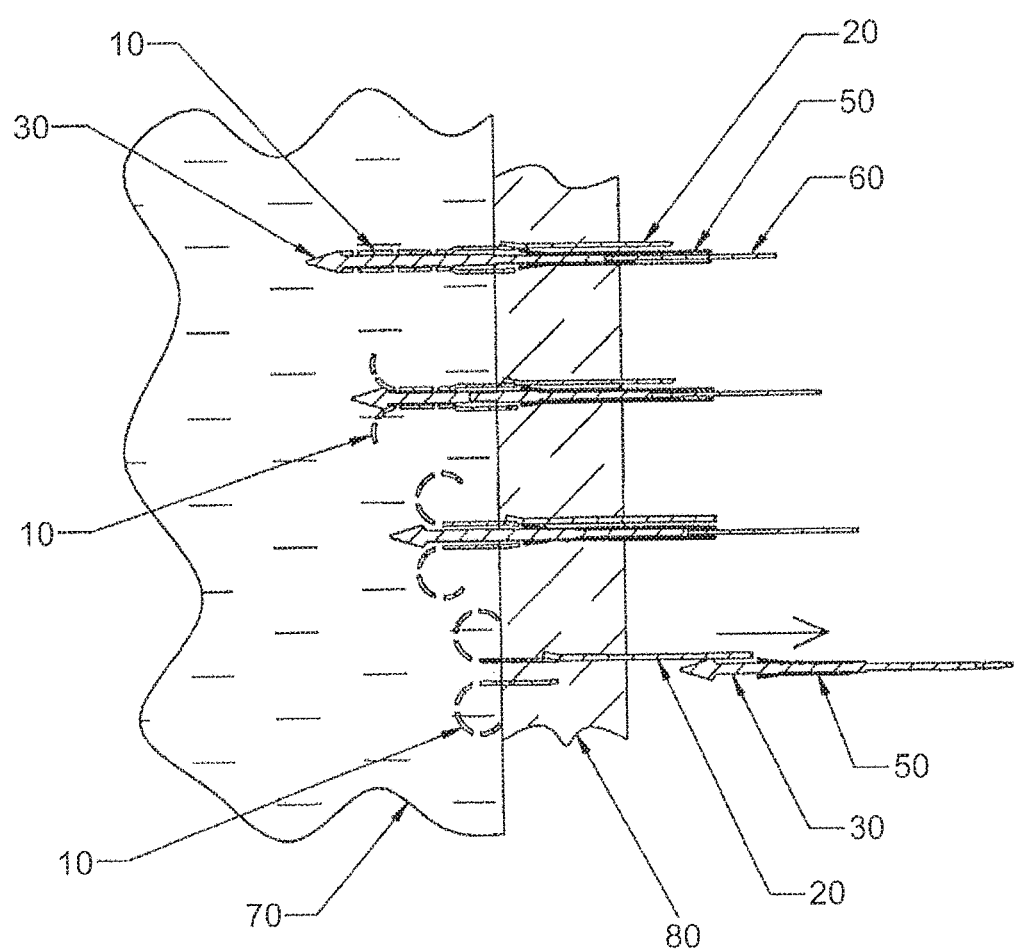
FIG. 6 is a four step side view partial cutaway drawing of an embodiment of the present invention in use.

FIG. 6 depicts the use of an embodiment of the present invention in four steps. In the first step (at top), the apparatus as a whole is shown as having been partially inserted through a first layer of tissue 80 (which may, for example be the bowel wall), and into a second layer of tissue 70 (which may, for example, be connective tissue outside the bowel wall). In the next three steps (proceeding downward), the expander 30 may be gradually retracted. This gradual retraction may force anchor 10 in its unexpanded state to partially expand. Eventually, the legs of anchor 10 may be fully expanded. In this instance, the anchor 10 may be retracted until it engages an outer surface of the first layer of tissue 80. A suture 20 may remain attached and extend through the first layer of tissue 80. The expander 30 and pusher 50 may be eventually completely withdrawn. In this instance the tether 60 may remain attached to the expander 30.

An alternative means of expanding the anchor 10 may be accomplished as follows. The anchor 10 may be constructed with legs made from a shape metal alloy, such as a nickel-titanium alloy. The legs may be pre-biased to assume an expanded state. However, the legs of the anchors may be maintained in an unexpanded state by means of a restraining sheath. Gradual retraction of the sheath may allow the legs to expand to their pre-biased expanded state. This mechanism may thus make use of the super-elastic properties of the shape-memory alloy. Alternatively, a temperature change memory effect of an alloy may also be used, by (for example) training the alloy into an expanded state, bending the legs into an unexpanded state, and then raising the temperature of the alloy above the necessary threshold to return it to the memorized expanded state. The temperature change may be accomplished by a variety of means such as the use of a heating element.

Figure 7:
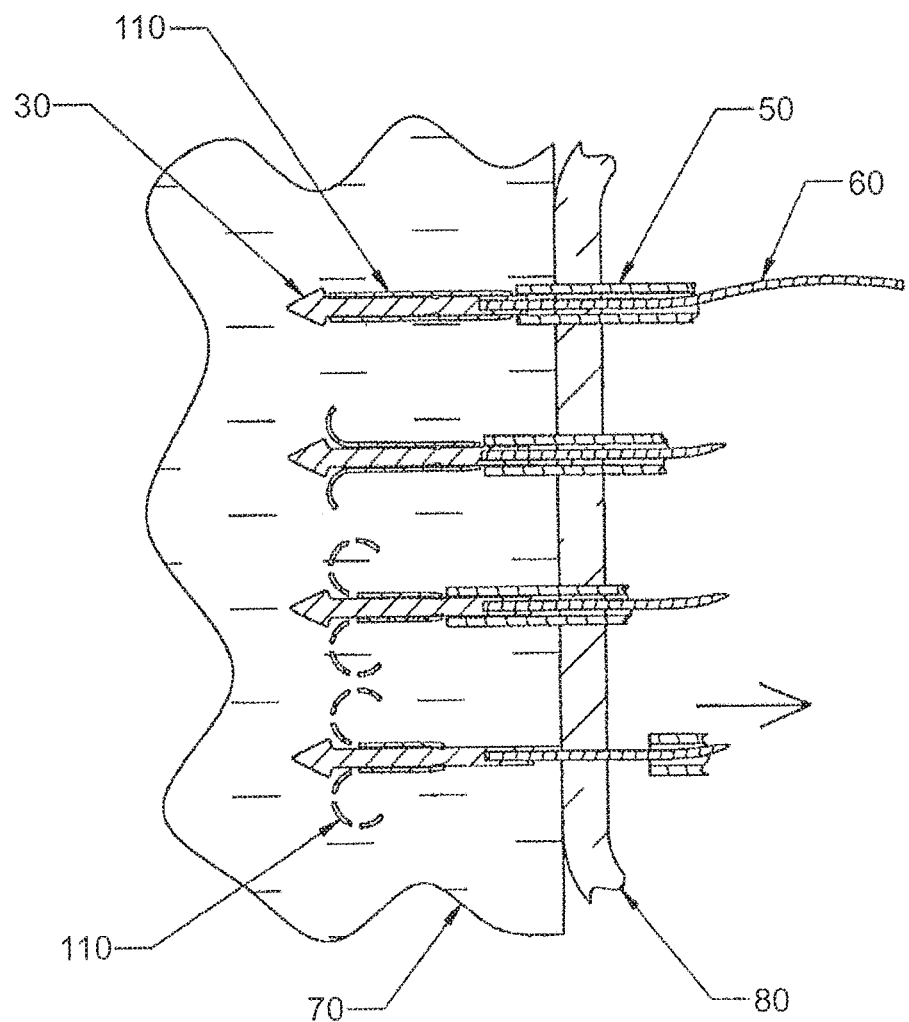
FIG. 7 is another four step side view partial cutaway drawing of an embodiment of the present invention in use.

FIG. 7 depicts another use of an embodiment of the present invention in four steps. In the first step (at top), the apparatus as a whole is shown as having been partially inserted through a first layer of tissue 80 (which may be, for example, the bowel wall), and into a second layer of tissue 70 (which may be, for example, a structure made of muscle tissue such as the diaphragm, and may, as shown here, be adjacent to the first layer of tissue 80). In the next three steps (proceeding downward), the pusher 50 may advance anchor 110 against expander 30. This advancement may force anchor 110 in its unexpanded state to partially expand, Eventually, the anchor 110 may be fully expanded. As shown, the anchor 110 may be left completely within the second layer of tissue 70. In this embodiment, the tether 60 and the expander 30 may remain partially within the second layer of tissue 70. For example, the expander 3 may lie completely with the second layer of tissue 70, and the tether 60 may remain attached and extend from the second layer of tissue 70, through the first layer of tissue 80. The pusher 50 may be withdrawn in a proximal direction. As previously discussed, the expansion may take place by any relative opposing motion of the expander and anchor. Additionally, an anchor may be deployed by prebiasing a leg to an expanded radius, constraining or constricting the leg to a narrower radius, and then removing the restraint. Such a technique may include the use of a superelastic leg constrained by a sheath. As the sheath is removed in, for example, a proximal direction, the leg may expand the distal radius of the anchor.

Figure 8:
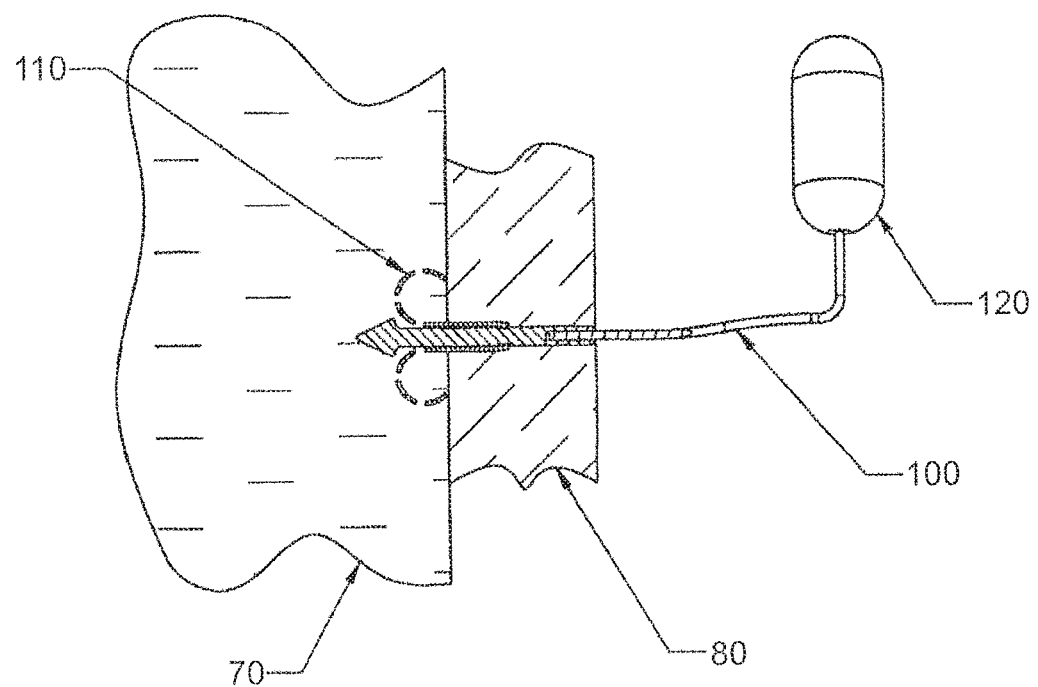
FIG. 8 is a drawing of an embodiment of the present invention including an anchor with an expander and a sensor or treatment delivery device attached to a tether.

FIG. 8 depicts an embodiment of the present invention including a sensor or treatment delivery device 120. in this embodiment, the anchor 110 may lie within a second layer of tissue 70. A tether 100, may pass through a first layer of tissue 80, and connect the anchor 110 with a sensor or treatment delivery device 120. Examples of sensors 120 include cameras, electromagnetic sensors, manometry sensors, pH probes, and probes for lumen content sampling. Example of treatment delivery devices 120 include pharmaceutical delivery devices; chemotherapy delivery devices; treatment activation devices (e.g. photodynamic therapy devices); radioisotope containment or delivery devices; thermal or radiofrequency delivery devices; radioisotope containers; thermal, photochemical, and radio frequency delivery devices; and stimulating electrode devices, including pacemakers and nerve stimulators. Attachment of the sensor or treatment delivery device 120 to tether 100 may be accomplished by, for example, a nail, screw, bolt, clip, knot, loop, friction mount, or adhesive mechanism. A tether may be a suture, but it may also be a more rigid material, and may be an inflexible material. Examples of materials that may serve as a tether include a wire.

Figure 9:
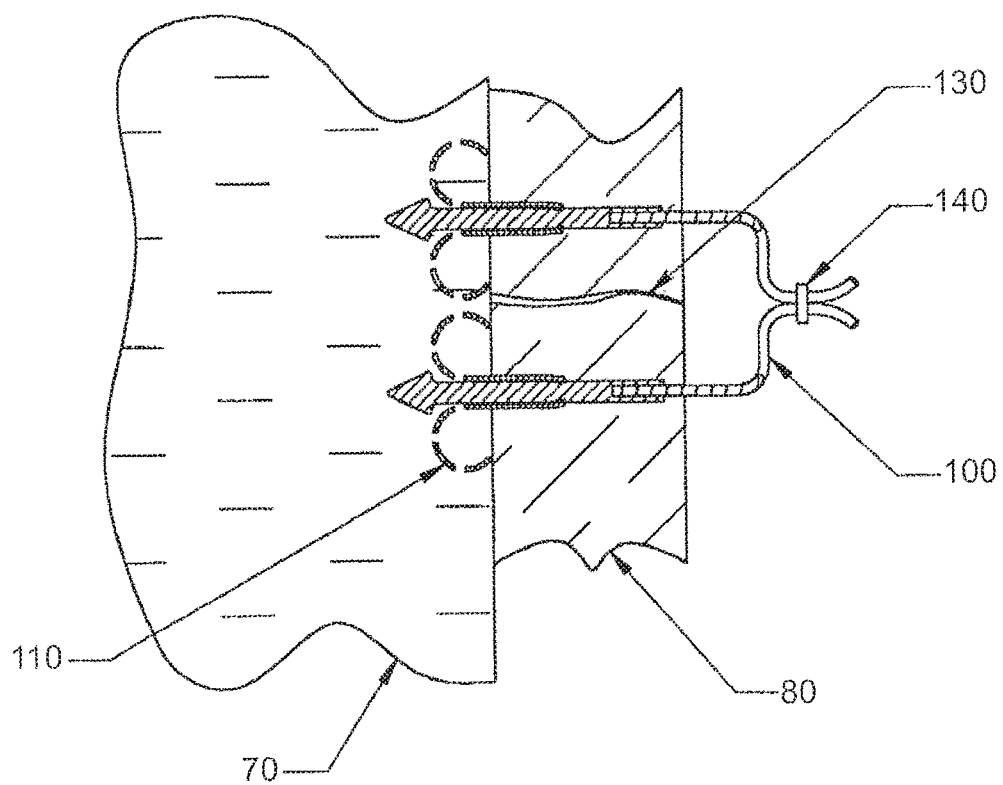
FIG. 9 is a drawing of an embodiment of the present invention including two anchors (with expanders) connected by two tethers.

FIG. 9 depicts an embodiment of the present invention including two anchors 110 connected by two tethers 100. In this example, the anchors and tethers may be inserted as previously described. However, the tethers 100 may further be connected by a lock ring 140. Drawing the tethers together may allow the margins of the first layer of tissue 80 and the second layer of tissue 70 to approximate and close a tear or gap in tissue continuity 130.

Figure 10:
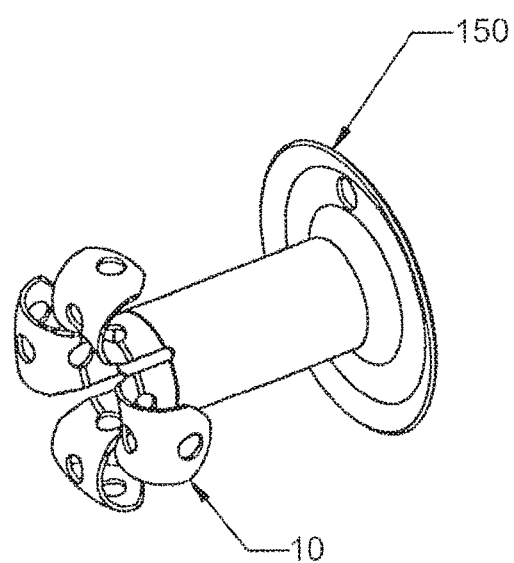
FIG. 10 is a drawing of an anchor with a shoulder.
Figure 11:
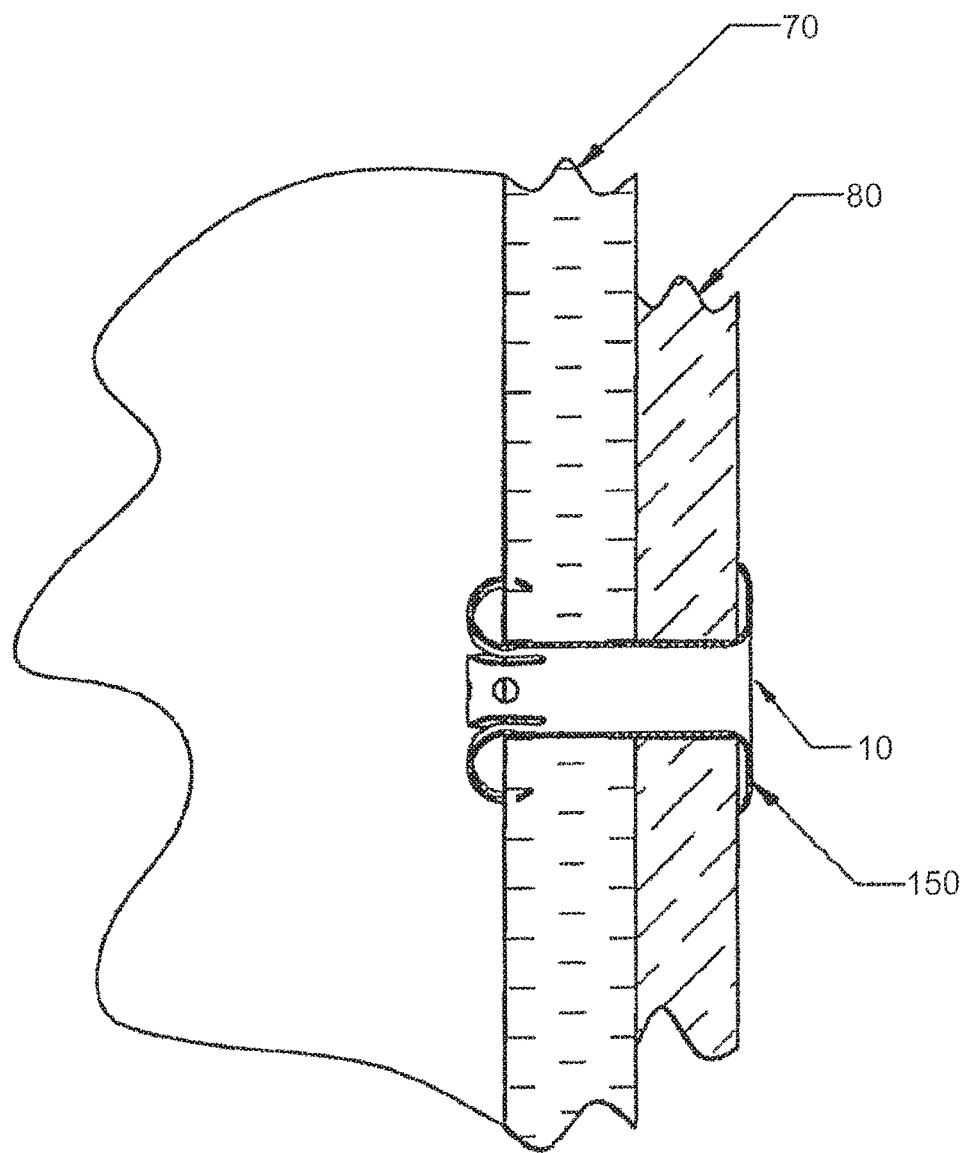
FIG. 11 is a cross-section drawing of an anchor with a shoulder that may serve as a stent.
Figure 26:
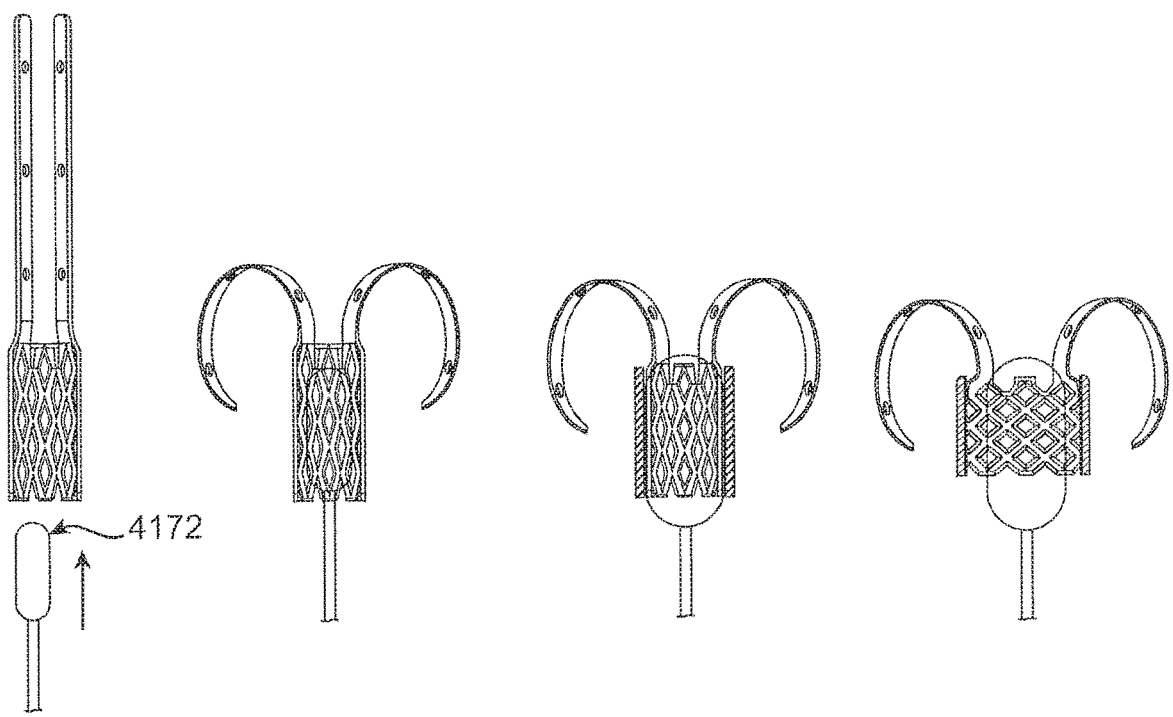
FIG. 26 is a four-step sectional view of an embodiment of the invention showing an inflatable balloon to expand a stent anchor.

FIG. 10 depicts an anchor 10 with a shoulder 150. In this embodiment of the present invention, an anchor 10 (shown expanded) may be provided with a shoulder 150. This shoulder 150 may be adapted to prevent over penetration by providing significant resistance to further penetration. FIG. 11 depicts an anchor 10 with a shoulder 150 passing through a first layer of tissue 80 and a second layer of tissue 70. In this example, the anchor 10 may be provided with a hollow center. Thus, when in place, as shown, the anchor 10 may serve as a stent. The stent may, for example, be self-expanding or mechanically expandable. A balloon may be used to expand the stent, and this may permit the stent to acquire an increased diameter as shown in FIG. 26. Tabs may be provided directed radially inwardly to convert some of the force of an expander moving in an axial direction into a radially expansive force on the stent.

Figure 12:
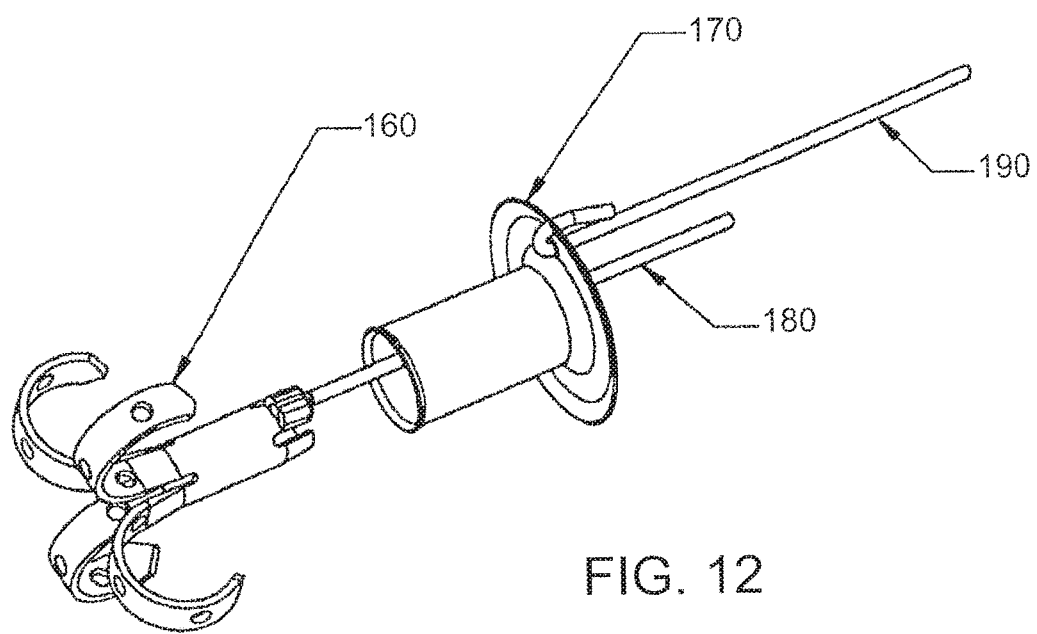
FIG. 12 is a drawing of an anchor with a separate shoulder.

FIG. 12 depicts an anchor 160 with a separate shoulder 170. In this embodiment, the anchor 160 and the shoulder 170 are in t\VO pieces. These pieces may be adapted to engage one another. This may be accomplished, for example, by providing the pieces with corresponding threads, by arranging for a light frictional fit, or by tensioning tethers 180 while advancing rod 190. One advantage of this design may be the ease of removal. In particular, the shoulder 170 may be restrained from moving in a proximal direction, and tension may be applied in a proximal direction to the anchor 160. This may force the anchor 160 through the shoulder 170 in a proximal direction, collapsing the anchor 160 in the process.

Figure 13:
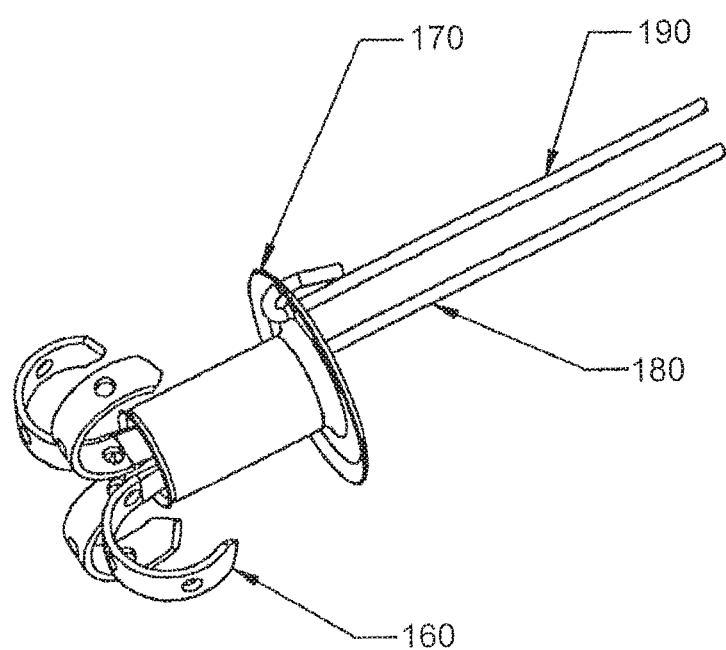
FIG. 13 is a drawing of an anchor with a separate shoulder installed on the anchor.

FIG. 13 depicts an anchor 160 with a separate shoulder 170 as installed. This anchor 160 is otherwise the same as FIG. 10. It is an object of the invention to provide a device that efficiently and effectively penetrates tissue in a precisely targeted manner for a diagnostic or therapeutic endoscopy or endosonography-guided transluminal procedures.

The present invention may be a puncturing or penetrating member that includes or is provided with a tissue anchoring or engaging member. The puncturing member may be integral with the tissue anchoring member. For example, a barbed needle would integrate both a tissue penetrating and tissue anchoring member. In another embodiment the members may be separate. For example, an anchor may be provided that may be fitted around a tissue penetrating member. The tissue penetrating member may also be adapted to be withdrawn in such a manner that it expands the distal radius of the anchor member. The anchoring member may involve such devices as crossbars, flanges, hooks, barbs, adhesive, or dips. The anchoring member may also be a gas or liquid inflatable element, such as a balloon. The puncturing member may be detachable by means of an elongate link such as a thread, wire, strand, or cord.

Figure 14:
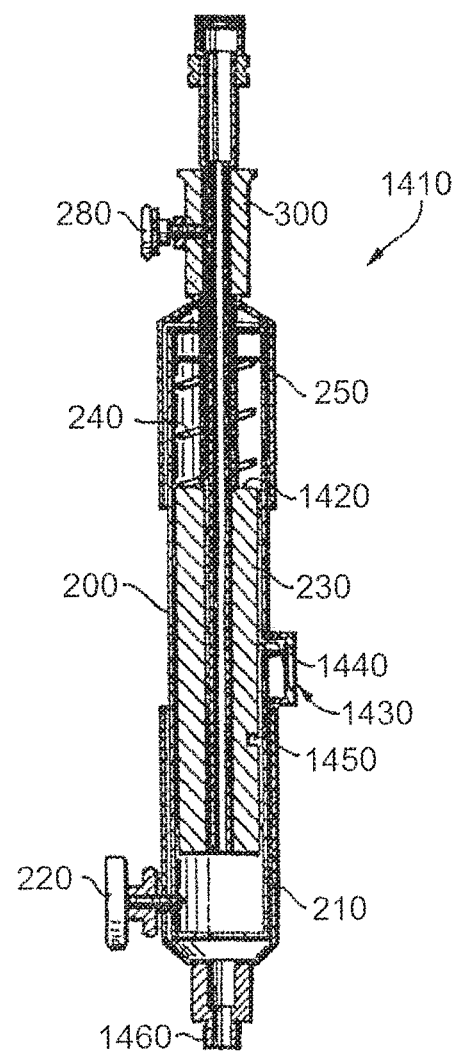
FIG. 14 is a drawing of an alternative embodiment of the present invention including a release device.

Referring to FIG. 14, such an embodiment of the present invention may include a tissue penetrating device, an outer sleeve 210, and a handle 1410. The handle 1410 may include a main cylinder 200 that houses a sliding piston 230, and a compression spring 240. The upper (proximal) end of the outer piston may have a shoulder above which the compression spring 240 may be loaded. In a particular embodiment, when the outer piston, is maximally advanced in the main cylinder 200, the compression spring 240 may be relaxed (as opposed to tightly compressed) and handgrip may be in contact with the calibrating sleeve. The outer piston may be retracted by pulling back on the handgrip, thereby loading the compression spring 240 by compressing it.

The main cylinder may be provided with a trigger that has a spring. Retraction of the outer piston may engage this spring in the groove, thereby locking the outer piston in the locked position. Pressing a button may release this lock, allowing the compression spring to uncoil (relax) and advance the outer piston distally at high velocity.

The handgrip may be provided with a screw that secures the position of the inner piston 230 that contains the tissue penetrating device. The calibrating sleeve may be adjusted proximally to shorten the distance that the outer piston will progress after the spring is released. Thus, the distance of the tissue penetrating device may be precisely calibrated. An outer sleeve 210 may be connected and secured to the main cylinder 200 with a screw. The outer sleeve 210 may be screwed into the instrumentation channel inlet port of the endoscope or echo-endoscope by screw attachment. The outer sheath 40 may screw into the main cylinder. By loosening the screws, the position of the outer sleeve 210 may be adjusted relative to the main cylinder 200. Such an adjustment may adjust the exposed length of the outer sheath 40.

Figure 15:
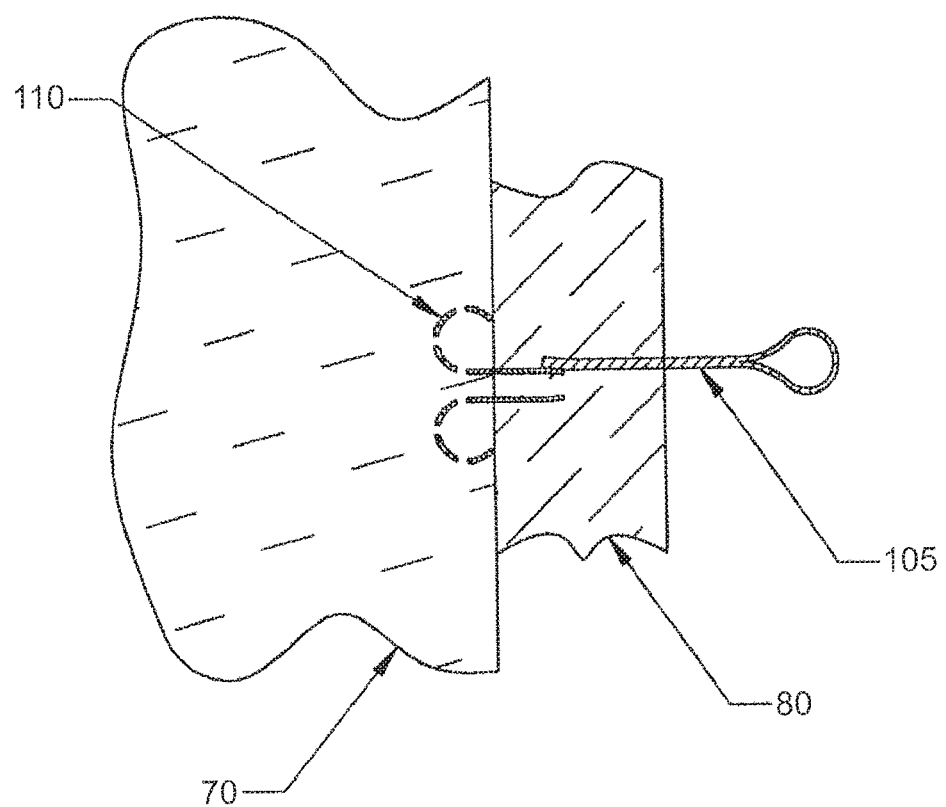
FIG. 15 is a drawing of an embodiment of the present invention including an anchor without an expander and further including a suture with a loop at the proximal end, with the loop optionally attached to a sensor or treatment delivery device.

FIG. 15 depicts an embodiment of the invention similar to that shown in FIG. 8. In this embodiment, the expander has been removed from the anchor 110. The suture 105 may be attached to the anchor 110 in a non-coaxial position. The suture may have a loop or other member at the proximal end which may be used to attach a sensor or treatment delivery device. It may be advantageous to remove the expander from the anchor 110 because the expander may be used to expand anchors at other locations. Attachable devices may include, for example, treatment activation devices (e.g. photodynamic therapy devices), radioisotope containment devices, radioisotope delivery devices, thermal delivery devices, or radio frequency delivery devices, Although the invention is described in terms of an expander, the expander may also be used for non-expansion purposes (such as to aid in penetrating tissue) and may (in some instance) not be used for any expansion purpose. For example, if a leg (or a plurality of legs) of shape memory alloy is used, the deployment mechanism may be the withdrawal or rupture of an encompassing sheath.

Figure 16:
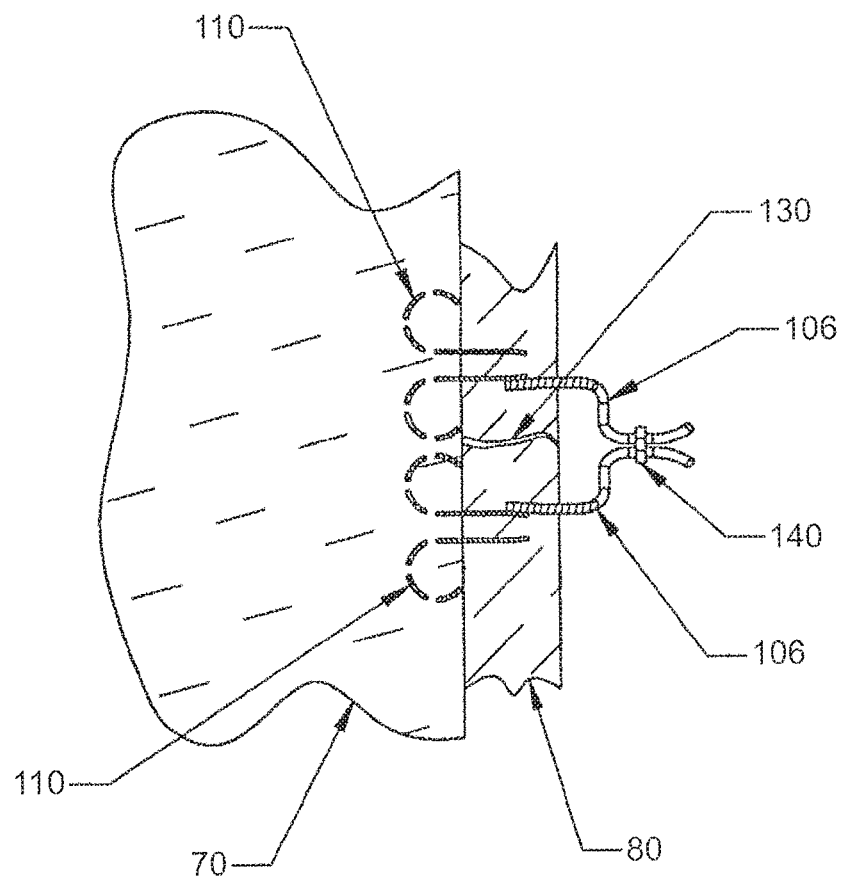
FIG. 16 is a drawing of an embodiment of the present invention including two anchors (without expanders) connected by two sutures.

FIG. 16 depicts an embodiment of the invention similar to that shown in FIG. 9. In this embodiment, the expanders have been removed from the anchors 110. The suture 106 may be attached to the anchor 110 in a non-coaxial position. It may be advantageous to remove the expander from the anchor 110 because the expander may be used to expand anchors at other locations. Sutures 106 may be connected by a lock ring 140.

Figure 17B:
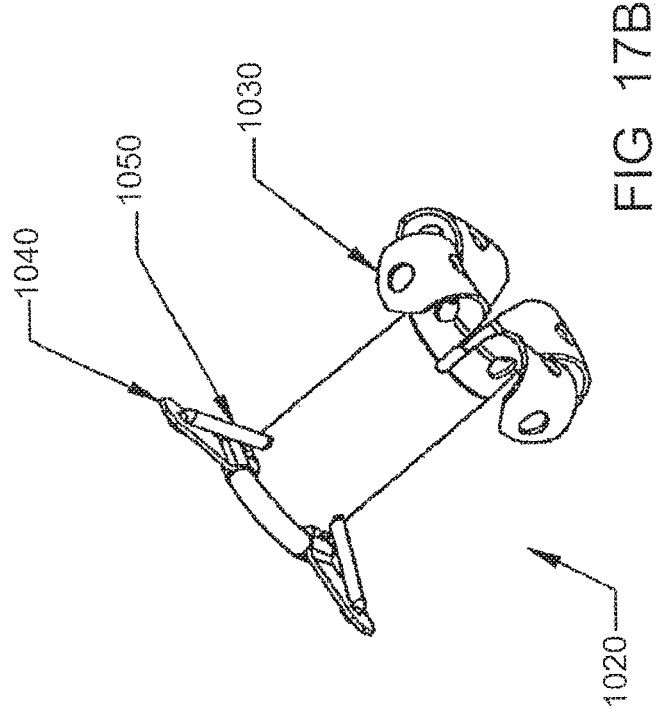
Figure 17A:
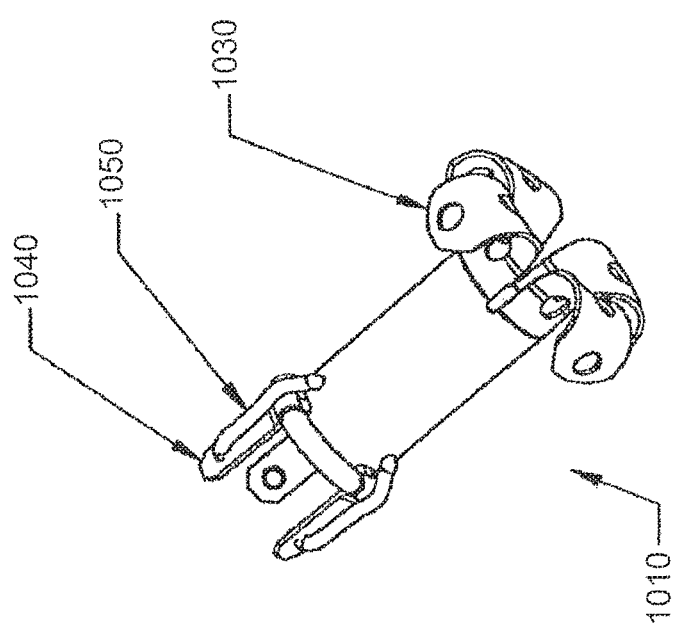

FIGS. 17A and 17B depict an anchor 1030 with a collapsible shoulder 1040. Anchor assembly 1010 shows the distal legs of an anchor deployed with a collapsible shoulder mechanism at the proximal end of the anchor in its pre-deployed position. Shoulder tabs 1040 pivot on the anchor 1030 and may be connected to the anchor 1030 with elastic tension members 1050 such as silicone rubber bands. An encompassing sheath (not shown) may prevent the shoulder tabs 1040 from deploying until it the encompassing sheath 1065 retracted. Once the sheath 1065 is retracted, the shoulder tabs 1040 on anchor assembly 1020 may be forced by the elastic tension members 1050 to deploy and form a shoulder that may prevent the distal motion of the anchor 1030. The distal legs (if more than one leg is used) may be implemented by a superelastic alloy, in such a configuration, the distal legs may be trained to produce an expanded distal radius, and may be constrained by the encompassing sheath 1065 to a narrower radius.

Such an arrangement may require fewer discrete components.

FIG. 18 depicts the use of the collapsible shoulder mechanism in two steps. In the first step (at top), the anchor 1030 is shown penetrating a first layer of tissue 1070 and a second layer of tissue 1080 with its legs already deployed. An encompassing sheath 1065 is shown in position restraining the opening of shoulder tabs 1040 against the applied force from the elastic tension member 1050. The next step depicts the retraction of the expander 1055 and its associated tether 1060 and the encompassing sheath 1065. These components may be retracted simultaneously or sequentially. The encompassing sheath 1065 may be removed first so that the expander 1055 and tether 1060 may stabilize the anchor 1030 prior to deployment of the collapsible shoulder. The encompassing sheath 1065 may be removed and the shoulder tabs 1040 may be forced into place against the second layer of tissue 1080 by the force supplied by elastic tension members 1050. As described elsewhere, the encompassing sheath 1065 may also deploy legs by releasing a constraint on the legs. Additionally, the encompassing sheath 1065 may be releasably attached to a distal portion of the legs. The distal portion of the leg may be slightly spooned inward, so that its distal portion extends slightly radially outwardly. As the sheath is retracted, the ends of the legs may be pulled in a proximal direction. This may cause the legs to form an approximately U-shaped configuration which may have the effect of expanding a distal radius of the device. At a suitable time, the encompassing sheath may release the legs after they have formed such a shape. For such a deployment, as with deployment by an expander, it may be advantageous to use a leg formed of a malleable material.

Figure 19:
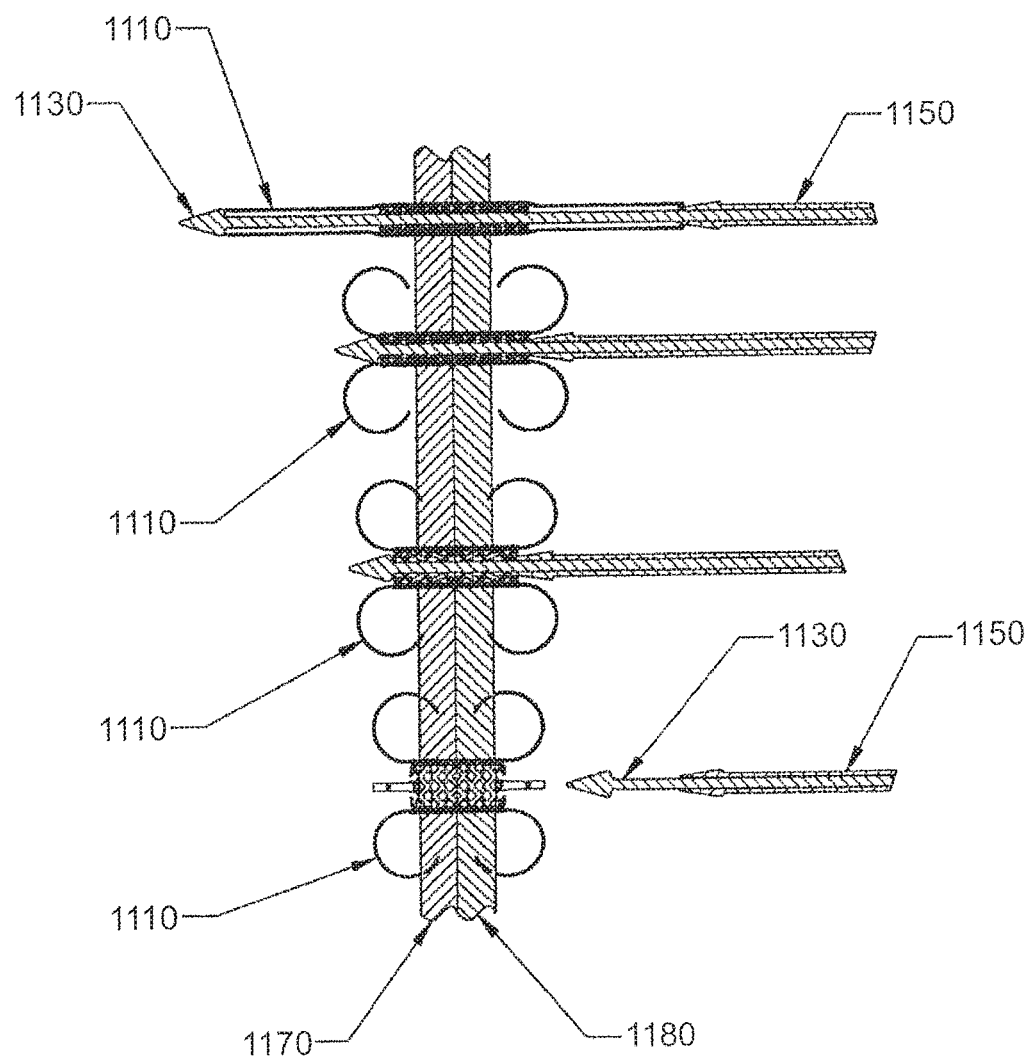
FIG. 19 is a four-step sectional view of an embodiment of the invention with an anchor that may serve as an expandable stent.

FIG. 19 depicts the use of an expandable stent in combination with an anchor. The figure shows a series of four steps of installing an anchor with an expandable stent In the first step (at top), the combination anchor with expandable stent 1110 may be inserted through two layers of tissue 1170 and 1180. An expander 1130 may be located coaxially within the anchor 1110. The expander 1130 may be retracted proximally by, for example, a tether (not shown). A pusher 1150 may be slipped over the expander 1130 and positioned coaxially with the expander 1130. The pusher 1150 may be used to counteract axial loads or forces applied by the expander 1130 to the anchor 1110 in a proximal direction. In the second step, the expander 1130 may cause the distal legs of the anchor to deploy. Simultaneously, the pusher 1150 may cause the proximal legs of the anchor to expand. The expander 1130 and pusher 1150 may then make contact with tabs in the anchor. This contact may prevent their further axial motion. Application of increased tensile force on the tether (not shown) connected to the expander 1130 and increased compression force on the pusher 1150 may load the anchor 1110 in compression.

The compression loading of the anchor 1110 may yield the material and cause plastic deformation. The anchor body may be formed of an open mesh-like structure that expands in diameter as it yields and is forced into a shorter axial configuration. The third step in the figure ii lustrates an intermediate point of expansion of the diameter. Finally, the fourth step depicts the anchor folly expanded and the expander 1130 and pusher 1150 retracted from the anchor 1110. It would also be possible to expand the stent portion of the anchor with an inflatable balloon. The expandable stent depicted in FIG. 19 could also be configured with a collapsible shoulder mechanism as illustrated in FIGS. 17 and 18. Such a stent may be made of a malleable material. Similarly, a stent may be made of a superelastic alloy. Such a stent may be constrained to a first diameter by an encompassing sheath (not shown) and may resume a larger diameter after the sheath is removed.

Figures 22A, 22B:
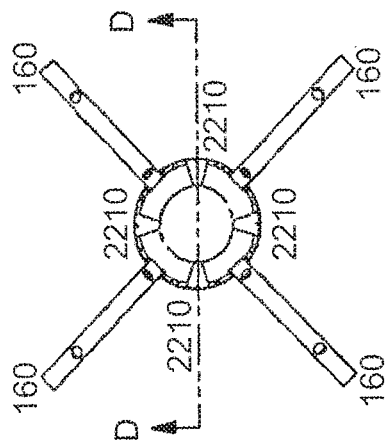
FIGS. 22A-H are detailed depictions of detailed views of an expandable stent in combination with an anchor.
Figure 22C:
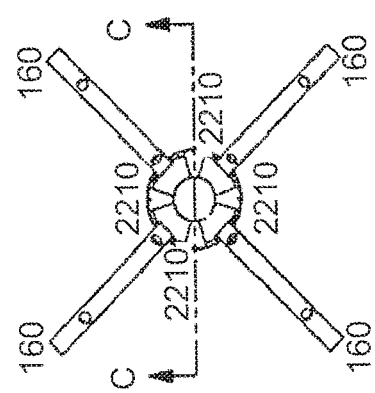
Figure 22D:
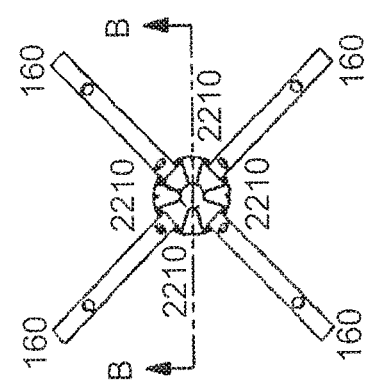
Figures 22E, 22F:
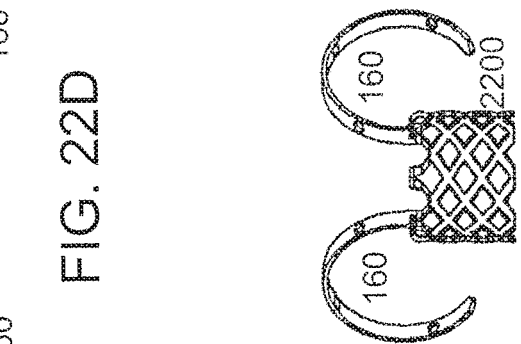
Figure 22G:
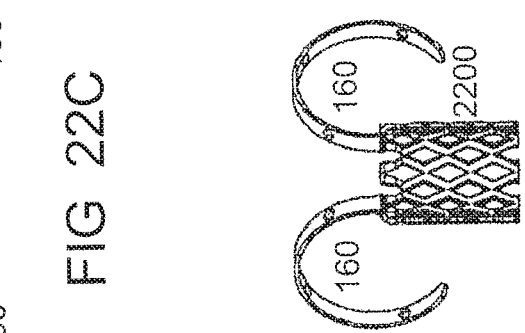
Figure 22H:
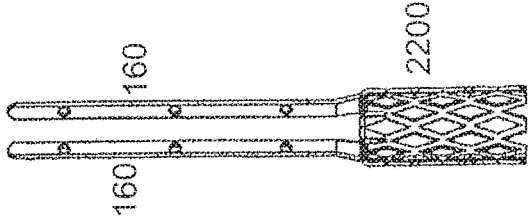

FIGS. 22A-H depicts detailed views of an expandable stent 2200 in combination with an anchor. Referring to FIGS. 22A and 22E (FIG. 22E is the sectional view A-A of FIG. 22A), the anchor may be delivered to the site with the legs 160 straight and the stent 2200 may initially be in an unexpanded state. Referring to FIGS. 228 and 22F (FIG. 22F is the sectional view B-B of FIG. 22B), the legs 160 may be deployed by means of the action of an expander device (not shown) moving coaxially through the anchor (from distal end towards proximal end). Referring to FIGS. 22C and 22G (FIG. 220 is the sectional view C-C of FIG. 22C), the stent 2200 diameter may be expanded. The expander that deployed the legs may also be used to expand the stent as well. Tabs 2210 may be formed on the stent 2200. Such tabs 2210 may be bent radially inward. Such a bend may catch the expander as it is pulled toward the proximal end of the anchor. Continued pulling on the expander may cause the stent 2200 to plastically deform. The mesh-like walls of the stent 2200 may cause the stent diameter to increase as the stent length is reduced by the compressive force applied through the expander. A pusher device, not shown, may counteract the force applied by the expander and may thereby keep the anchor stationary. The stent 2200 may approximately double in diameter (compare FIGS. 22A and 22D). In another configuration the diameter may increase more than double. The reduction in length with increased diameter is also illustrated in FIGS. 22D and 22H (FIG. 22H is the sectional view D-D of FIG. 22D). Also compare FIGS. 22E and 22H. The coaxial expander may be used (if desired) to perform a pali of the expansion (or none at all). Other ways to effectuate the expansion of the stent 2200 include using a shape-memory alloy such as Nitinol that may be pre-biased to the expanded state. The unexpanded stent 2200 may be constrained in a sheath that may be retracted once in the stent is in the proper position. Another way to expand the stent 2200 is to deform the stent 2200 into a larger diameter using an inflatable balloon.

Figure 20:
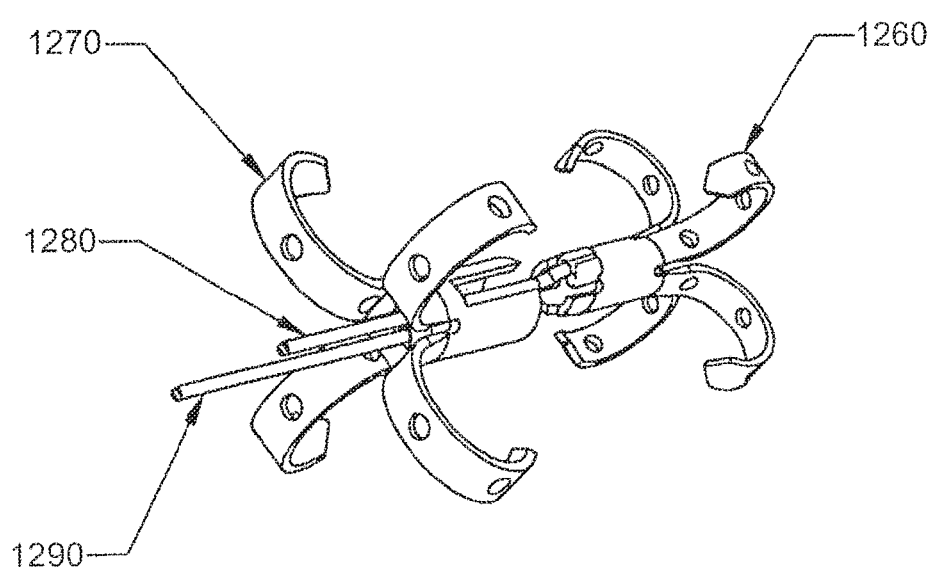
FIG. 20 is a perspective view drawing of an embodiment of the present invention with an anchor with a separate expandable shoulder.
Figure 21:
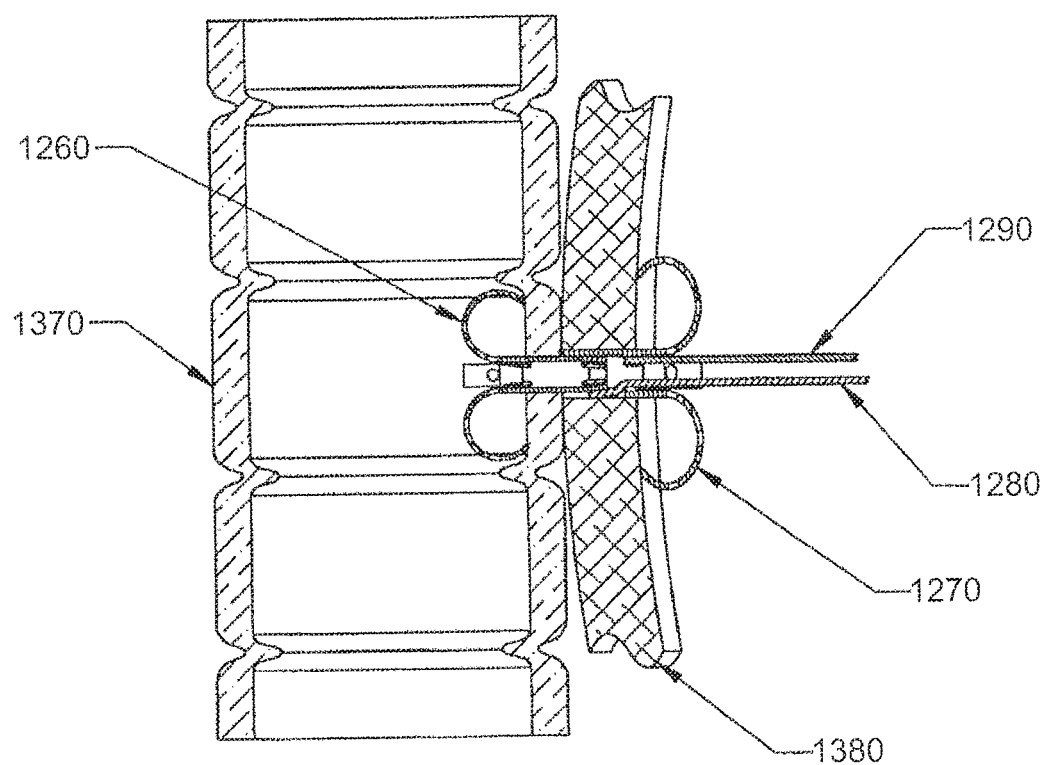
FIG. 21 is a sectional view drawing of an anchor (with an expandable shoulder) situated in a portion of bowel and securing another luminal tissue structure to the bowel.

FIG. 20 depicts an anchor 1260 with a separate expandable shoulder 1270. In this embodiment, the anchor 1260 and the shoulder 1270 are two separate pieces. The pieces may be adapted to engage each other. This may be accomplished as described above for the configuration shown in FIG. 12. Tethers 1280 and 1290 may be provided for applying tension to the anchor 1260 and compression to the expandable shoulder 1270. The expandable shoulder 1270 may have its legs deployed in the same fashion as described earlier for deploying the legs of an anchor. An expander (not shown) may be forced between the legs of the expandable shoulder 1270 in a distal direction, and this forced movement may expand the legs. FIG. 21 depicts the embodiment of the invention shown in FIG. 20 installed between the stomach 1380 and section of bowel 1370 to create an anastomosis.

Automatic operation of the penetrating device and pre-biasing the penetrating device may occur via use of for example, a mechanical spring. Other pre-biasing devices may include, for example, compressed air or chemical explosion. In the example of a spring biasing device, as soon as the spring is released, the penetrating device may thrusts forward into a layer of tissue. By virtue of the greater inertia of the mass of the endoscope (if one is used in conjunction with the present invention), the penetrating device may experience all (or almost all) of the relative motion and may pass through even hardened tissue. The high velocity of the penetrating device may lessen the bending of the penetrating device and may help to overcome the striction effects. More specifically, according to the device of the present invention, the penetrating device pre-biased may rush forward after a release (or launch) device provided with the pre-biasing device is operated. Further, the use of the penetrating device of the invention may result in avoiding the potentially undesirable (in certain circumstances) repeated reciprocating motion that may be required by conventional techniques and devices. In this case, the penetrating device that may be located in the passage formed in the endoscope may be surrounded by a protecting sleeve. The sleeve may be made of an impenetrable material that may be moved independently of the penetrating device. The movable sleeve may protect and may reinforce the penetrating device and may position the penetrating device appropriately, even after the penetrating device has moved out of the passage provided in the endoscope.

In order to reliably move the penetrating device forward and to prevent the pre-biasing device from projecting, the housing of the pre-biasing device may be set into screw engagement with the opening of the passage provided in the endoscope. Adjusting means (such as, for example, screws or slides) may precisely adjust the position of the penetrating device and the forward movement of the pre-biasing device.

Referring to FIG. 14, the penetrating device may include an operating and pre-biasing device. The device may have a main cylinder 200 in which a sliding piston 230 may be provided, The sliding piston 230 may have a projection 1420 on its top end. To the projection 1420 there may be attached a spring 240 fix pre-biasing the penetrating device. A release device 1430 having a spring 1440 may be provided on the main cylinder 200. The spring 1440 may be set into a groove 1450 made in the slide piston, when the penetrating device or the slide piston 230 is biased. At the end of the slide piston 230, which may be distant from the penetrating device, a grip 300 may be provided to move the piston 230, thereby performing automatic penetration. On the grip 300 a stop pin 280 may be provided, by which the penetrating device may be secured. As long as the spring 240 is released, the grip 300 may remain in contact with a calibration cap 250. The position of the calibration cap 250 may be changed to adjust the end position of the piston 230 and hence the penetration depth of the penetrating device.

An outer sleeve 210 may be provided on the end of the main cylinder 200, which may be near the penetrating device. This end of the cylinder 200 may hold the pre-biasing and control device in the penetrating device passage provided in the endoscope. The main cylinder 200 may be fastened to the outer sleeve 210 by means of a stop pin or screw 220. The outer sleeve 210 may be fixed in the open end (inlet port) of the penetrating device passage of the echo-endoscope by means of a screw attachment 1460. Standard endoscopes and "interventional" echo-endoscopes can be used. Using an interventional echo-endoscope, the angle of departure of the penetrating device may be adjusted at the echo-endoscope. The transducer at the end of the echo-endoscope may be surrounded by a latex balloon. The latex balloon can be filled with water during the use of the echo-endoscope. The water can serve as a medium between the detection probe and, for example, the intestinal wall.

The penetrating device may extend through an outer sheath that may be made, for example, of a flexible metal weave or impenetrable plastic. The penetrating device may be inserted into the endoscope by the operating- and pre-biasing device until it projects, along with the sleeve, from the lower end of the endoscope. In certain cases, it may be desired that the penetrating device tip be beveled and that the distal end of the penetrating device be sand-blasted, pitted, or otherwise altered to improve the resolution of ultrasonic imaging.

A dull stylet may be located in a hollow penetrating device (in some situations in which a hollow penetrating device is desired) and may be flush with or may project by approximately 2 mm from the open end of the penetrating device. The proximal end of the penetrating device, which may be ready for insertion into the operating and pre-biasing device, may be set in screw engagement with the proximal end part of the operating and pre-biasing device.

In the device according to the invention, the penetrating device can be manually moved back and forth by loosening the stop pin provided on the grip. The position of the penetrating device can therefore be manually adjusted. Referring to FIG. 14, the slide piston 230 may be drawn back greatly. If so, the groove 1450 may move toward the spring 1440, compressing the coil spring 240. When the spring 1440 comes into engagement with the groove 1450, the penetrating device may be pre-biased and can be quickly moved forward by the release device 1430. The calibrating sleeve 250 may adjust the depth of penetration of the penetrating device. A coarse adjustment may be possible in accordance with the depth of insertion of the main cylinder 200. At this stage in the use of the device, the main cylinder 200 may be fixed in place by stop pin or screw 220. A quick and accurate adjustment of the penetrating device may be performed by manipulation of the outer sleeve 210 provided at the end of the main cylinder 200. Once the stop pin or screw 220 is loosened, while the stop pin 280 at the grip remains tightened, the protective sheath attached to the main cylinder 200 and the penetrating device secured to the slide piston may be inserted together into the outer sleeve 210 until they become visible by the endoscope. Thereafter, the stop pin or screw 220 may be tightened, whereby the calibrating sleeve 250 may adjust the depth of penetration with precision. The stylet (if one is used, a stylet is not required for the present invention) may be drawn a little from the hollow penetrating device, releasing the sharp end of the hollow penetrating device. The sharp end of the penetrating device first penetrates a first layer of tissue, such as the intestinal wall, and then comes close to a second layer of tissue that is to be punctured.

As soon as the penetrating device reaches the tissue to be punctured, the stylet may be removed and may be replaced by any device or substance that may be set into contact with the other end of the hollow penetrating device. The stop pin 280 provided on the grip 300 may be loosened to insert the penetrating device into the tissue to be punctured. To accomplish manual puncture, the stop pin 280 may be loosened and the penetrating device may be moved back and forth with respect to the main cylinder 200. When the manual puncture is difficult to achieve or when the tissue is hard to penetrate, the release device 1430 may release the elastic spring 240. Thus, the penetrating device may project forward into the hardened tissue.

Regarding one goal of this invention, the automation of the installation of anchors, one skilled in the art should recognize that it is possible to further automate the installation of anchors. As shown in FIG. 3, for example, it is possible to have multiple anchors staged near the distal end of the apparatus. The installation device may, thus, be readily modified to provide a cocking action that compresses the spring, retracts the pusher member through the next anchor and advances a next anchor and pusher member toward the expander.

Figure 23:
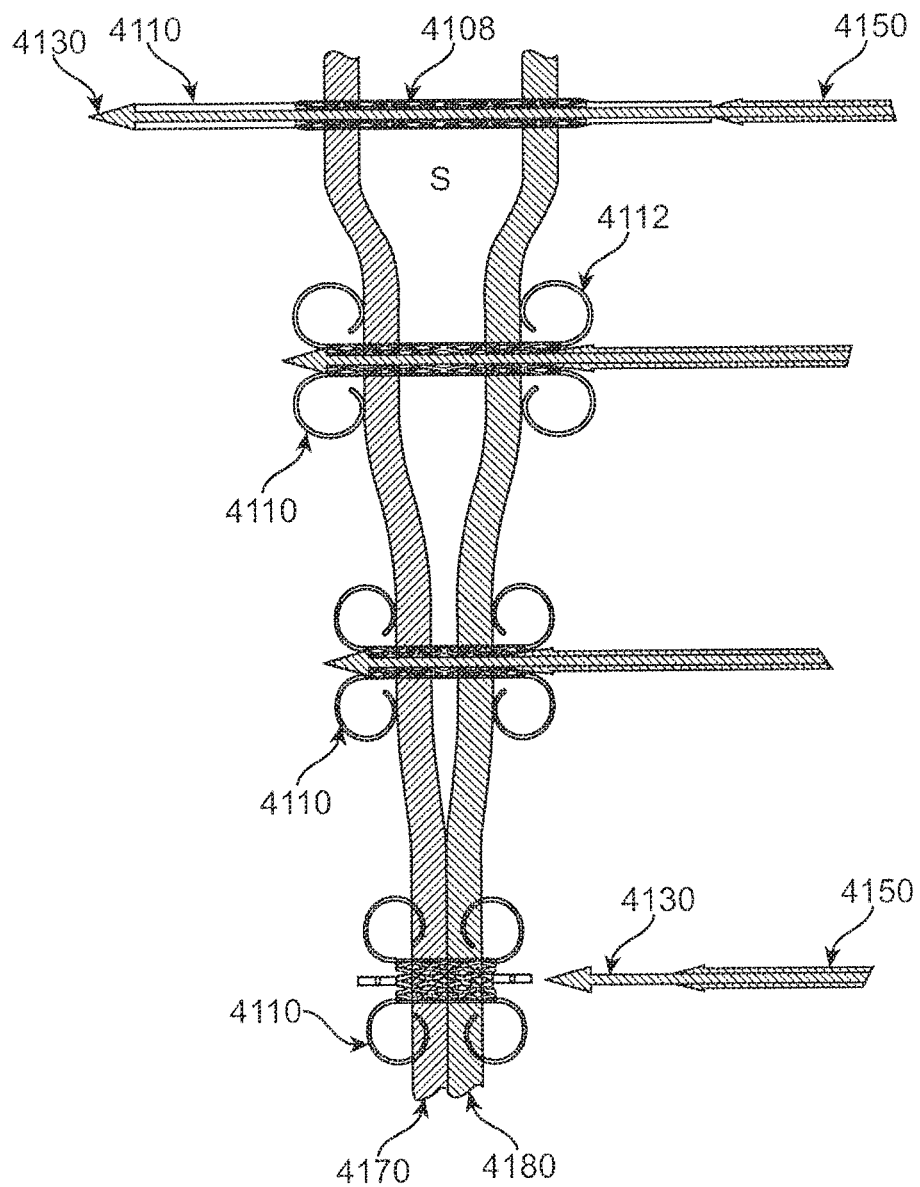
FIG. 23 is a four-step sectional view of an embodiment of the invention with an anchor that may be used to approximate luminal structures and serve as an expandable stent.

As shown in FIG. 23, the device according to an alternate embodiment of the invention may be used to approximate two luminal structures a conduit in between. The device depicts the use of a central member 4108 that has a distal anchor 4110, or sometimes referred to as a distal retention member, coupled at the distal end of the central member. The central member 4108 also may have a proximal anchor 4112, or sometimes referred to as a proximal retention member, coupled at the proximal end of the central member. The figure shows a series of four steps of installing these anchors with a central member. The central member 4108 may be an expandable member that is capable of shortening in length as it expands in diameter. Examples of such expandable member may be deformable stents, self-expanding stents, expandable meshes, or Nitinol shape memory material that expands in response to a heat source either body temperature or through applied resistance heat The central member 4108 may be a conduit that is adapted to transfer fluid from one end of the central member to the other. In the first step (at top), the expandable central member 4108 with coupled anchor 4110 may be inserted through two layers of tissue 4170 and 4180 that are part of first and second luminal structures. These luminal structures may be separated by a space S. One example of these types of luminal structures may be the stomach and the gall bladder which may be positioned next two one another or be separated by a distance inside the abdominal cavity. An expander 4130 may be located coaxially within the central member 4108 and the anchors 4110 and 4112. The expander 4130 may be retracted proximally by, for example, a tether (not shown). A pusher 4150 may be slipped over the expander 4130 and positioned coaxially with the expander 4130. The pusher 4150 may be used to counteract axial loads or forces applied by the expander 4130 to the anchor 4110 in a proximal direction. In the second step, the expander 4130 may cause the legs of the distal anchor to deploy. When the expander 4130 is retracted proximally, the substantially straight legs of the distal anchor curl radially outwardly causing an increase in the diameter of the anchor. The legs may partially curl or may fully curl. When the legs are fully curled, a substantially round ring like shape is formed as shown in steps 2 and 3. This fully curled condition may be useful to present an anchor interface with the tissue that reduces trauma to the tissue. In the case of partial curling, the legs may be used to actually penetrate the tissue layers 4170 and 4180. This partially curled position may be useful to secure the anchor to the tissue layer. Simultaneously, the pusher 4150 may cause the legs of the proximal anchor to expand. When the pusher 4150 is advanced distally, the substantially straight legs of the proximal anchor curl radially outwardly causing an increase in the diameter of the anchor. The legs may partially curl or may fully curl. The expander 4130 and pusher 4150 may then be used to apply a further axial compression force through the tabs in the anchor.

In one embodiment of the invention this axially applied compression force may be used to draw the two luminal structures closer together thereby reducing the space S between the luminal structures by shortening the effective longitudinal length of the central member. This is illustrated in the second and third steps. This approximation of luminal structures may be useful to reduce the distance between structures to facilitate fluid exchange between the two or to improve the accessibility of these structures by positioning therapeutic instruments into one from the other. In step four, the walls of the structures are shown side by side each other but this amount of approximation may not be necessarily required.

Continued application of increased tensile force on the tether (not shown) connected to the expander 4130 and increased compression force on the pusher 4150 may load the central member 4108 in compression which may also cause further deformation of the central member resulting in an enlargement of the central member diameter. This increase in diameter may be useful to increase fluid exchange between the two luminal structures or to allow larger sized instruments such as scopes into the second luminal structure. Although the process of decreasing the central member length to approximate the luminal structures and increasing the diameter to increase fluid flow and accessibility may occur separately, these processes may also occur sequentially or even simultaneously depending on the design of the central member.

Figure 24:
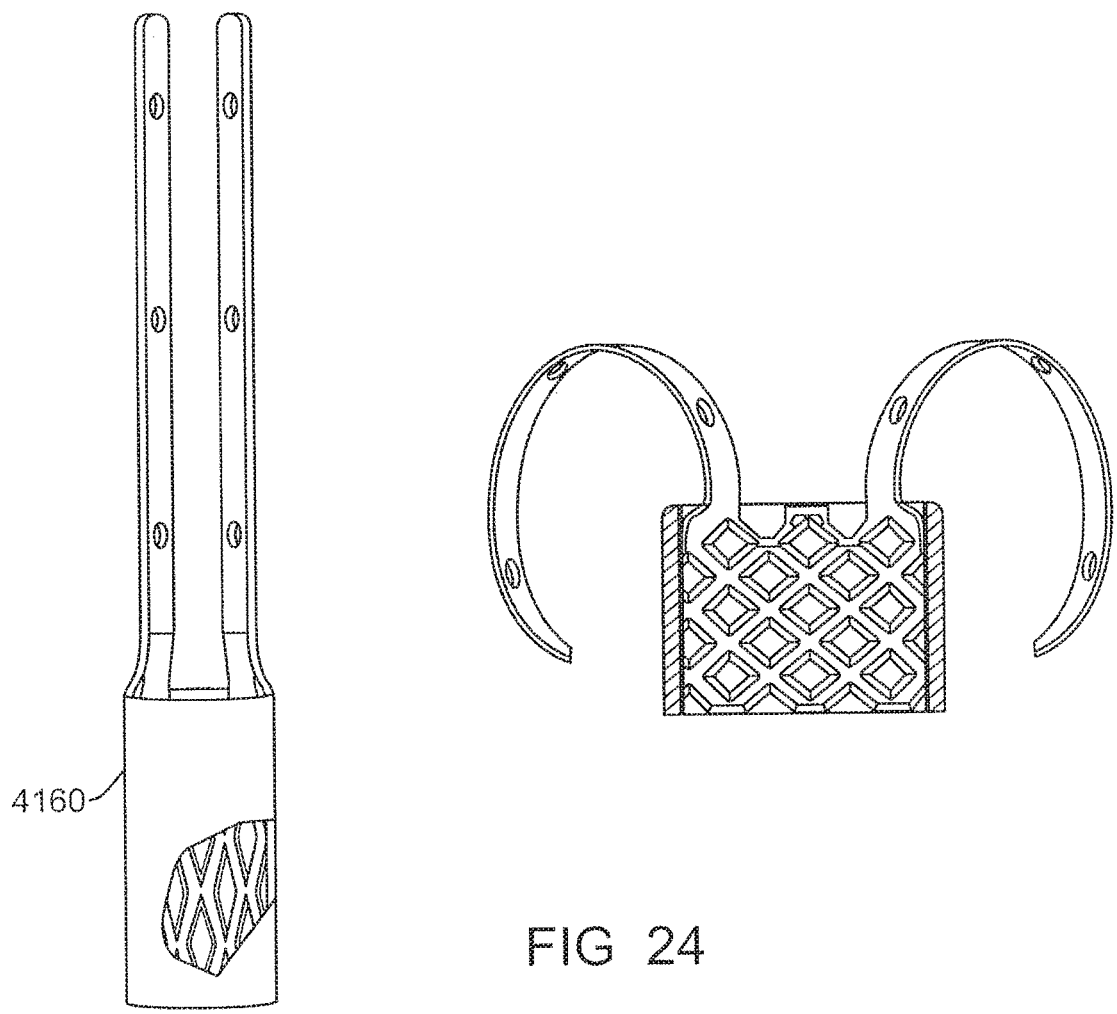
FIG. 24 is a sectional view showing an anchor with an expandable central member having a covering.

The central member may have a thin covering or membrane 4160 disposed about it that is designed to seal the central member to provide a fluid conduit that inhibits fluid leaks between the fluids of the luminal structures and the fluids of the abdominal cavity or other anatomical spaces. This is depicted in FIG. 24. It is preferred that when the central member and the anchors are fully deployed that a stable fluid conduit is established so that fluids may pass from one luminal structure to another without significant loss of fluid. The covering 4160 may be an elastic covering that can expand or contract as the central member expands and contracts, if the central member is an expandable stent, the covering should be designed to seal the gaps between the braids of the stent thereby sealing the outside of the stent and making the stent internal diameter capable of conduction fluids. Although in Figures.

Figure 25:
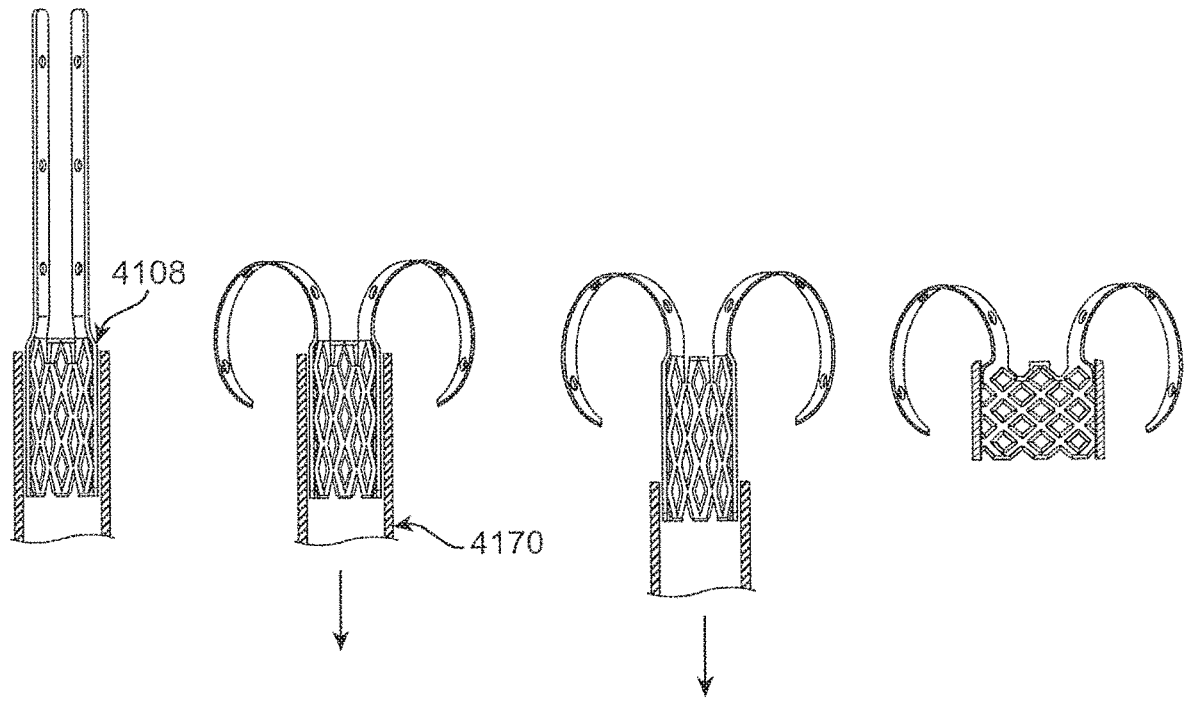
FIG. 25 is a four-step sectional view of an embodiment of the invention with a restraining member covering a self expanding stent.

As shown in FIG. 25, the expandable central member 4108 may be a self-expanding stent or mesh that is constrained in a small diameter configuration and then self-expands as a restraining member is removed. The self-expanding member is shown restrained by an encompassing sheath 4170. As the encompassing sheath 4170 is withdrawn the expandable central member 4108 enlarges to an expanded condition with a diameter that is larger than the restrained configuration. Such expansion may be accompanied with a concomitant shortening of the member length along the longitudinal axis.

As shown in FIG. 26, the expandable central member 4108 may be an expanding stent or mesh that must be expanded by the use of a dilating balloon 4172. The dilating balloon 4172 may be positioned inside the stent and with the balloon in a deflated condition. Once inside the stent or mesh the balloon 4172 may be inflated to expand the diameter of the member as shown in the third and fourth steps. Once the member is sufficiently expanded, the balloon may be deflated and withdrawn leaving behind a central expanding member with an expanded inside diameter.

Alternately the expandable central member 4108 may be an expanding stent or mesh that is constructed from a metal alloy material such as Nitinol that expands from a first diameter to an expanded diameter by the exposure to body heat or by applying a current to the mesh or stent such that raises the temperature of the metal alloy so that a programmed shape may form. An alternative embodiment of the invention is illustrated in FIG. 27. This device is similar to that previously described in FIG. 20. This device illustrates two separate anchors 1260 and 1270 which are both coupled to central members 1271 and 1272 respectively. The central members 1271 and 1272 are coaxially aligned such that central member 1271 is slidably positioned inside central member 1272. This device is designed to allow for variable functional distances between anchors 1260 and 1270. After the anchors 1260 and 1270 are positioned in or about the first and second luminal structures respectively and the anchors are expanded as shown in FIG. 27, the two luminal structures may be approximated by drawing the two anchors 1260 and 1270 close to each other. As the anchors and thereby the luminal structures are approximated, the central member 1271 slides inside central member 1272 and the distance between the anchors 1260 and 1270 decreases. The central members may be provided with a ratcheting mechanism (not shown) that permits selective anchor to anchor separation distances. In this embodiment the approximation of the luminal structures may controlled by the operator. This may be preferable because the amount of approximation possible for one situation with one set of luminal structures may be different from another situation. This embodiment may allow the operator to decide the optimal luminal structure spacing in situ and reduce the amount of further interventions required. Once the optimal spacing is determined, the two central members may lock in position together by utilizing various locking apparatus well known to those skilled in the art. Such locking mechanisms may include bayonet locks, compression locks such as by twisting one central member relative to the other, tab and slot or other mechanisms. If a device such as this is removed, the two central members may be unlocked from each other and the smaller central member 1271 removed from the first luminal structure. The second central member 1272 may be subsequently removed by collapsing the anchor 1270 and removing the device from the second and the first luminal structures.

As described above, it may be necessary to remove a device that has been positioned across two luminal structures. In one method a grasper may be introduced to the proximal end of the central member or to the proximal anchor coupled there. The grasper may grasp the proximal anchor and pull proximally. This axial force may pull the central member proximally and the distal anchor coupled to it. Sustained axial displacement of the grasper may cause the distal anchor to uncurl as the central member is withdrawn. The grasper may finally remove the device from the tissue layers.

Figure 28:
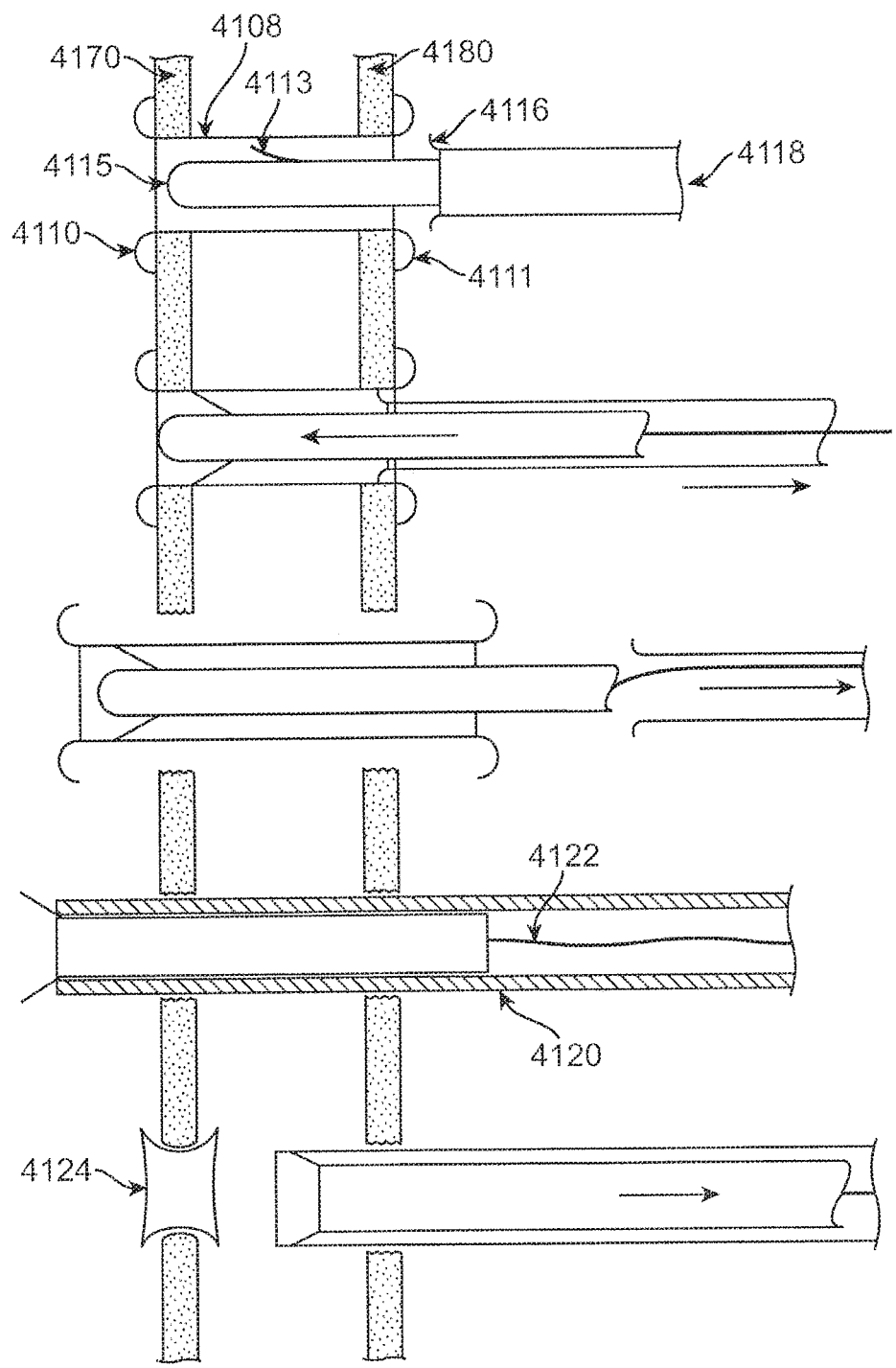
FIG. 28 is a five-step perspective view of an embodiment of the invention including a method to remove an anchor.

Another embodiment of the present invention is illustrated in FIG. 28 that is designed to permit removal of a device once deployed. As shown in the first illustration of FIG. 28, the device is deployed from a first luminal structure across wall 4180 and across wall 4170 and into a second luminal structure. This deployment is similar to that previously described in FIG. 23. The device has been deployed such that the two walls 4170 and 4180 have been approximated, anchors 4110 and 4111 have been expanded and are deployed at or into the walls as shown and the central member 4108 is in an expanded condition. The expanded device may be removed by the introduction of a removal device having a distal probe 4115 which has a foldable barb 4113 positioned on at least one side of the probe sidewall near the distal tip of the probe. The foldable barb is collapsed flush with the outside wall of the probe for introduction and can be made to unfold to at least a 30.degree.angle. A proximal probe 4118 is concentrically positioned about the distal probe 4115 and has at least two hooks 4116 coupled to the distal end of the proximal probe 4118. These hooks are configured to attach to the proximal end of the device near the proximal anchor 4111.

As shown in the second step of FIG. 28, the removal device is positioned inside the expanded central member and the proximal probe is attached to the proximal end of the central member near the proximal anchor 4111. In the case where the central member is a stent, the hooks 4116 of the proximal probe may for example ensnare the braids of the stent. The distal probe is brought near the distal opening of the expanded central member and the foldable barbs are deployed such that they impinge on the inside walls of the central member. If the central member is an expanded stent, the barbs are designed to wedge against the sidewall of the stent. In this configuration the removal device is ready to begin removal of the expanded central member 4108. The distal probe 4115 is advanced distally as shown by the arrow in the second step illustration. Simultaneously the proximal probe 4118 is withdrawn proximally in the direction of the arrow shown in the second step illustration. This action applies a tensile force on the expanded central member and deforms and stretches the expanded central member so that the length of the central member increases and the diameter subsequently decreases. This may move the central member away from the walls of the luminal structures as the central member lengthens and the diameter decreases. It is understood that minimal stretching of the central member may be required to facilitate its removal and the walls 4170 and 4180 may collapse around the central member as it is stretched. The central member should be stretched sufficiently so that the anchors 4110 and 4111 may be extricated from their respective walls 4170 and 4160. Once the anchors are separated from the walls, which may be visible using direct endoscopic visualization or using ultrasound or other diagnostic methods, the proximal anchor 4111 is removed or detached from the proximal end of the central member 4108. A collapsing sleeve 4120 is then slid over the distal probe 4115 and advanced over the probe 4115 until the distal anchor 4110 contacts the collapsing sleeve 4120. The position of the distal probe 4115 may be maintained as the collapsing sleeve is advanced distally by applying a tensile force to a tether 4122 attached to the proximal end of the distal probe. As the collapsing sleeve is further advanced the legs of the distal anchor 4110 are straightened and contained within the collapsing sleeve 4120. Finally, the collapsing sleeve 4120, distal anchor 4110 and the central member 4108 may be removed together.

Alternatively the device may be constructed with materials that are known to be bioabsorbable such that after a certain period of time, the device including the anchors and the central member may be reabsorbed by the body. This type of device may have several distinct advantages. This type of device does not require subsequent interventions to remove it after a period of time. This is less invasive and potentially safer and more comfortable for the patient. Secondly as the device begins to break down slowly, it is probable that the first and second luminal structures will repair the opening in their walls naturally as the device degrades so that a plug or patch is not required.

The walls of the first and second luminal structures may collapse as the collapsing sleeve 4120 is withdrawn to occlude the opening created by the central member. However, in another embodiment, a plug 4124 may be deposited in any remaining opening to artificially occlude the opening. This may be important to limit the amount of fluids that escape out of the luminal structures. This plug 4124 may also be a patch or a stopper. Alternatively, the opening may also be closed through the use of other well-known closure devices such as staples, sutures, or adhesives.

Figure 29:
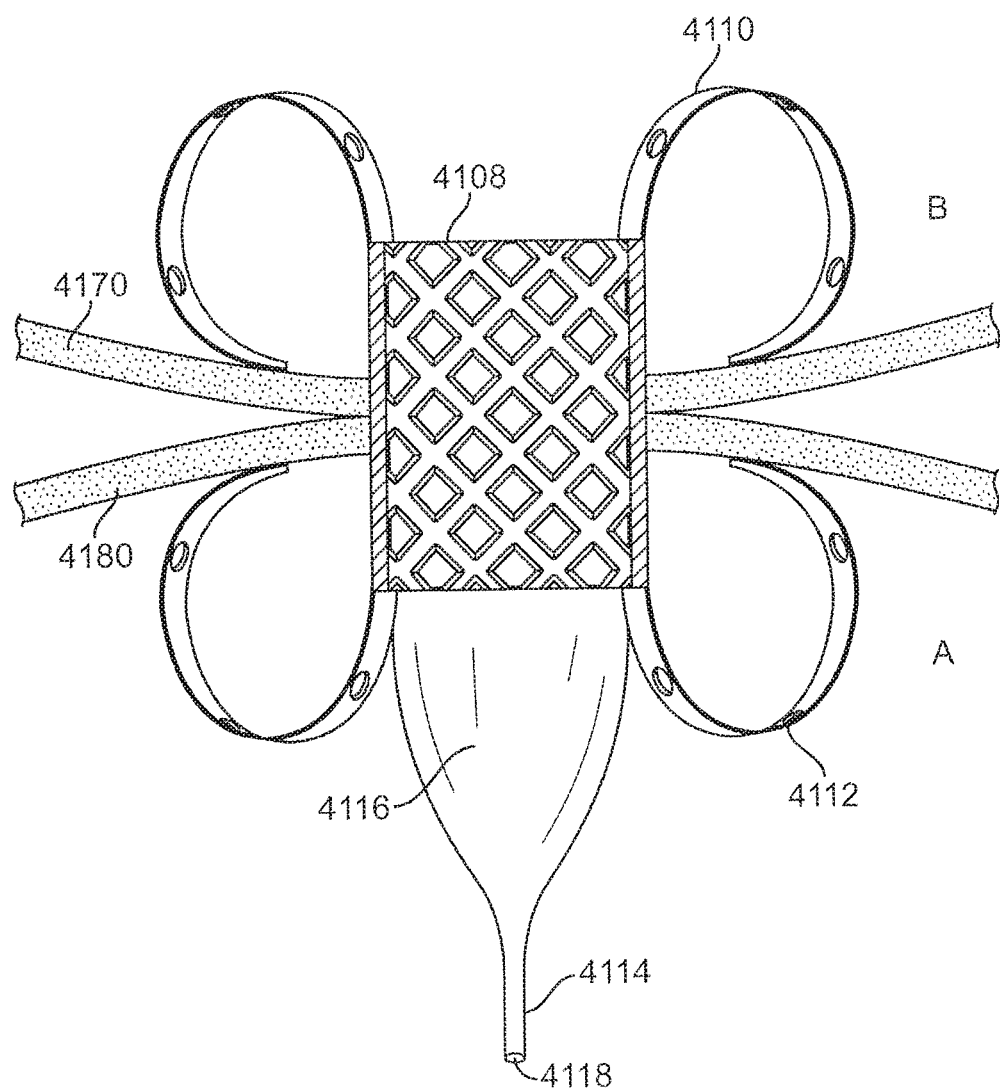
FIG. 29 is a perspective view of a collapsible valve member.

As shown in FIG. 29, the device may have a valve member 4116 that is attached to the proximal end of the central member 4108. The valve is a sock like member that is designed to restrict fluid flow to one direction. Preferably the valve member 4116 prevents fluid flow from the first luminal structure A to the second luminal structure B. The valve member may act similarly to a wind sock or a one way±lap valve in that the valve functions because the diameter of the proximal end of the valve, the neck 4114, is collapsed as compared to the diameter where the valve attaches to the central member to a small closed neck. The proximal tip 4118 has an opening so that instruments can be passed through the valve 4116 and into the second luminal structure B. The valve is capable of opening to accommodate passing instruments through it but quickly closes once these instruments are removed to restrict fluid flow to a single direction. The preferred direction of fluid flow is from the second to the first luminal structure although this could be reversed if necessary without affecting the function of the device.

This invention has been described and specific examples of the invention have been portrayed. The use of those specifics is not intended to limit the invention in anyway. Additionally, to the extent that there are variations of the invention, which are within the spirit of the disclosure or equivalent to the inventions found in the claims, it is my intent that this patent will cover those variations as well.

The invention claimed is:

1. A medical device for forming a fluid pathway, comprising:
a hollow member defining a longitudinally extending lumen configured to receive a penetrating member of a delivery catheter for deployment of the medical device, the hollow member comprising:
an expandable anchor at a distal end of the hollow member, and
a shoulder at a proximal end of the hollow member,
the expandable anchor configured to move from a first configuration to a second configuration such that:
a length of the hollow member decreases when in the second configuration, and
the expandable anchor radially expands into one or more curved surfaces when in the second configuration, the one or more curved surfaces configured to atraumatically engage a first tissue,
wherein the shoulder is configured to engage a second tissue to providing resistance to further penetration of the hollow member into the first tissue.

2. The medical device of claim 1, wherein the shoulder comprises a plurality of legs deployable from a first collapsed configuration to a second expanded configuration.

3. The medical device of claim 2, wherein the plurality of legs are biased to the expanded configuration.

4. The medical device of claim 1, wherein the expandable anchor comprises a plurality of legs, the plurality of legs disposed straight along a longitudinal axis of the hollow member when in the first configuration, the hollow member configured to receive an expander device, the expander device configured to bend the plurality of legs into the one or more curved surfaces to transition the hollow member from the first configuration to the second configuration.

5. The medical device of claim 4, wherein the plurality of legs are radially separated around a circumference of the hollow member.

6. The medical device of claim 4, wherein the expander device and the penetrating member are the same.

7. The medical device of claim 1, wherein the expandable anchor and the shoulder are two distinct pieces and are configured to engage with each other to form the hollow member.

8. The medical device of claim 1, wherein a central portion of the hollow member comprises a woven filament braid.

9. The medical device of claim 1, wherein the hollow member is configured to create an anastomosis between two body lumens, and wherein the first tissue is a tissue wall of one of the two body lumens.

10. The medical device of claim 1, wherein the one or more curved surfaces is generally transverse to an axis extending longitudinally through the lumen.

11. A system for forming a fluid pathway, comprising:
a penetrating member for deployment of a hollow member; and
a hollow member defining a longitudinally extending lumen configured to receive the penetrating member, the hollow member comprising:
an expandable anchor at a distal end of the hollow member, and
a shoulder at a proximal end of the hollow member,
the expandable anchor configured to move from a first configuration to a second configuration such that:
a length of the hollow member decreases when in the second configuration, and
the expandable anchor radially expands into one or more curved surfaces when in the second configuration, the one or more curved surfaces configured to atraumatically engage a first tissue,
wherein the shoulder is configured to engage a second tissue to providing resistance to further penetration of the hollow member into the first tissue.

12. The system of claim 11, wherein the shoulder comprises a plurality of legs deployable from a first collapsed configuration to a second expanded configuration.

13. The system of claim 12, wherein the plurality of legs are biased to the expanded configuration.

14. The system of claim 11, wherein the expandable anchor comprises a plurality of legs, the plurality of legs disposed straight along a longitudinal axis of the hollow member when in the first configuration, the hollow member configured to receive an expander device, the expander device configured to bend the plurality of legs into the one or more curved surfaces to transition the hollow member from the first configuration to the second configuration.

15. The system of claim 14, wherein the plurality of legs are radially separated around a circumference of the hollow member.

16. The system of claim 14, wherein the expander device and the penetrating member are the same.

17. The system of claim 11, wherein the hollow member is configured to create an anastomosis between two body lumens, and wherein the first tissue is a tissue wall of one of the two body lumens.

18. A drainage device, comprising:
a cylindrical member defining a lumen for passage of fluid, the cylindrical member receivable over a penetrating member of a delivery catheter for deployment of the drainage device, the cylindrical member comprising:

an expandable anchor at a first end of the cylindrical member, and a shoulder at a second end of the cylindrical member, the expandable anchor configured to move from a first configuration to a second configuration such that:

a length of the cylindrical member decreases when in the second configuration, and the expandable anchor radially expands into one or more curved surfaces when in the second configuration, the one or more curved surfaces configured to atraumatically engage a first tissue, wherein the shoulder is configured to engage a second tissue to providing resistance to further penetration of the cylindrical member into the first tissue.

19. The drainage device of claim 18, wherein the shoulder comprises a plurality of legs deployable from a first collapsed configuration to a second expanded configuration.

20. The drainage device of claim 18, wherein a central portion of the cylindrical member comprises a woven filament braid.

* * * * *